United States Patent [19]

Harvey, III

[11] Patent Number: 4,711,943

[45] Date of Patent: Dec. 8, 1987

[54] HYDROPHILIC SILOXANE MONOMERS AND DIMERS FOR CONTACT LENS MATERIALS, AND CONTACT LENSES FABRICATED THEREFROM

[75] Inventor: Thomas B. Harvey, III, Scottsdale, Ariz.

[73] Assignee: Sola U.S.A. Inc., Phoenix, Ariz.

[21] Appl. No.: 727,501

[22] Filed: Apr. 26, 1985

[51] Int. Cl.$^4$ .................. C08F 130/08; C08F 230/08
[52] U.S. Cl. ...................................... 526/279; 523/107
[58] Field of Search ................. 523/107; 526/279; 556/420

[56] References Cited

U.S. PATENT DOCUMENTS

| | | | |
|---|---|---|---|
| Re. 31,406 | 10/1983 | Gaylord | 526/279 |
| 2,929,829 | 3/1960 | Morehouse | 260/448.2 |
| 3,249,461 | 5/1966 | TeGrotenhuis | 117/76 |
| 3,652,629 | 3/1972 | Fort | 556/420 |
| 3,925,178 | 12/1975 | Gesser et al. | 204/165 |
| 4,136,250 | 1/1979 | Mueller et al. | 528/29 |
| 4,139,513 | 2/1979 | Tanaka et al. | 260/29.6 TA |
| 4,139,548 | 2/1979 | Tanaka et al. | 260/448.2 B |
| 4,139,692 | 2/1979 | Tanaka et al. | 526/218 |
| 4,153,641 | 5/1979 | Deichert et al. | 260/827 |
| 4,182,822 | 1/1980 | Chang | 526/264 |
| 4,189,546 | 2/1980 | Deichert et al. | 528/26 |
| 4,216,303 | 8/1980 | Novicky | 528/32 |
| 4,235,985 | 11/1980 | Tanaka et al. | 526/279 |
| 4,254,248 | 3/1981 | Friends et al. | 526/279 |
| 4,259,467 | 3/1981 | Keogh et al. | 526/279 |
| 4,260,725 | 4/1981 | Keogh et al. | 526/279 |
| 4,276,402 | 6/1981 | Chromecek et al. | 526/264 |
| 4,277,582 | 7/1981 | Mueller et al. | 525/421 |
| 4,277,595 | 7/1981 | Deichert et al. | 528/26 |
| 4,343,927 | 8/1982 | Chang | 526/262 |
| 4,495,361 | 1/1985 | Friends et al. | 526/279 |
| 4,508,916 | 4/1985 | Newell et al. | 556/420 |

Primary Examiner—Peter F. Kulkosky
Attorney, Agent, or Firm—Charles E. Cates; David A. Lowin

[57] ABSTRACT

A monomer for making a contact lens with improved oxygen permeability and stability is disclosed as having a first portion for increasing wettability and a second portion for increasing oxygen permeability. The first portion includes a side-chain functionality of the structural formula:

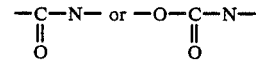

and is hydrophilic. The second portion includes a siloxane moiety, and is usually hydrophobic.

Also disclosed is a cross-linking agent, a polymeric material for making contact lenses, a method for making the polymeric material, and a method for making contact lenses from the material.

73 Claims, No Drawings

HYDROPHILIC SILOXANE MONOMERS AND DIMERS FOR CONTACT LENS MATERIALS, AND CONTACT LENSES FABRICATED THEREFROM

BACKGROUND OF THE INVENTION

1. Field of the Invention

The present invention relates to contact lenses. Particularly, the invention pertains to monomers and dimers for making contact lens materials, and to contact lens materials and contact lenses made therefrom. Specifically, the monomers and dimers of the invention include an amide and a siloxane in their structures. The invention also relates to a process for making the above-described monomers, dimers, contact lens materials, and contact lenses.

2. Background of the Invention

Up until about January 1982, the contact lens market consisted of basically three types of contact lenses: rigid non-gas permeable lenses [for example, made of poly-methylmethacrylate ("polyMMA")], gas-permeable rigid lenses (for example, made of silicone-containing monomers), and daily wear hydrogels (for example, made of poly-hydroxyethyl methacrylate). Since then, a new type of contact lens, an extended wear soft lens, has begun to penetrate the market and is having major impact on the future of the contact lens industry.

All of the extended wear contact lens materials that have been approved by the FDA to date can be characterized as high water content hydrogels. High water content hydrogels are not, however, viewed as being the "ultimate" polymer for the fabrication of extended wear contact lenses because of inherently weak physical properties. Also, the large polymer pore size of these high water content polymers usually leads to the formation of protein deposits that oftentimes penetrate into such lenses.

Hydrogel contact lenses tend to be weak, subject to deposit formation when worn in the eye, and lower in visual acuity than rigid contact lenses. All of these tendencies increase as the water content of the gels increase to the hydration levels required to obtain the degree of oxygen permeability needed for extended wear.

Rigid lenses, on the other hand, are less comfortable than hydrogel lenses. In a modern rigid lens, oxygen permeability is usually provided by siloxanes incorporated into the polymer. Siloxanes are usually hydrophobic by nature; siloxane-containing lenses have required wetting additives or surface coatings to provide adequate wettability for contact lens use.

Several approaches have been taken in the prior art toward solving the problem of wetting in oxygen permeable contact lenses made from siloxane polymers. Essentially all of the prior approaches have involved incorporation of a hydrophilic element in the polymer or copolymer system, to offset the hydrophobic nature of the siloxane.

Surface treatment, for example by generating free radicals through electrical discharge and subsequent attachment of polar radicals (including $NH_2$) is proposed in the Gesser U.S. Pat. No. 3,925,178. Such surface treatments (i.e. replacement of surface hydrophobic atoms and groups with polar hydrophilic functional groups) have a tendency to be short-lived in their effectiveness due to normal wear and tear on the surface.

Copolymerization of a variety of hydrophobic siloxane monomers having a glycerolethyl functionality in the sidechain, with a hydrophilic monomer (such as N-vinyl pyrrolidone or dimethyl acrylamide), a methacrylic acid alkyl ester monomer, a cross-linking agent and an initiator, are described in a series of patents to Tanaka et al. (U.S. Pat. Nos. 4,139,513; 4,139,548; 4,139,692; and 4,235,985). The Tanaka et al. references do not teach or suggest the acrylamide sidechain siloxane monomers and copolymers of the present invention.

The copolymerization of hydrophilic amide group-containing monomers (eg. N,N-dimethyl acrylamide) with a polysiloxanylalkyl ester of acrylic or methacrylic acids is taught by Chang in U.S. Pat. Nos. 4,182,822 and 4,343,927. This does not teach or suggest the acrylamide sidechain siloxane monomers and copolymers of the present invention.

Difunctional acrylic siloxanes are at the heart of what is called the B&L (Bausch & Lomb) technology, exemplified by U.S. Pat. Nos. 4,153,641; 4,189,546 and 4,277,595 (to Deichert et al.); 4,254,248 (to Friends et al.); 4,259,467 and 4,260,725 (to Keogh et al.); and 4,276,402 (to Chromecek et al.). There, a variety of polysiloxanes, end-capped with polymerizable unsaturated groups, are shown to be useful for manufacturing contact lenses without the use of "fillers" such as cross-linking agents. The specifications of such patents suggest (but no specific teaching nor example is provided showing) incorporation of an acrylamido group adjacent each polymerizable unsaturated group of the difunctional monomers and specifically teach away from use of monofunctional monomers, as requiring such "fillers". Moreover, even in the disclosed difunctional embodiments (including the macromolecules), the tetrakis-(trisubstituted siloxy)disiloxane dimers of the present invention are not shown nor suggested.

Similarly, Mueller et al. (in the U.S. Pat. Nos. 4,136,250 and 4,277,582) describes difunctional macromolecules, for copolymerization with a water soluble monofunctional molecule [such as N-(hydroxymethyl) acrylamide.] Incorporation of an amide adjacent each polymerizable unsaturated group of the difunctional non-hydrophilic macromer is suggested, but no examples are specifically provided. Likewise, the tris-(tri-substituted siloxy)disiloxane dimer of the present invention is not shown nor suggested.

Morehouse, in U.S. Pat. No. 2,929,829 describes a process for the production of organosilicon acylamino compounds, including a proposed N-[tris(triethoxy)-silylpropyl]acrylamide product, using gamma-amino-propyl triethoxysilane as a theoretical starting material. There is, however, no teaching nor suggestion of the tris-(tri-substituted siloxy)silylalkyl (meth)acrylamide monomers or copolymers of the present invention, nor is there any indication that such compounds would have any utility as contact lens materials.

Incorporation of an amide between an acrylate and a siloxane is shown in U.S. Pat. No. 3,249,461 (to Te-Grotenhuls) as the reaction product of gamma amino-propyl trimethoxysilane and methacryloyl chloride. The suggested use for the product is as an adhesive; nowhere is usefulness as a contact lens material taught. The tris-(tri-substituted siloxy)silylalkyl (methy)acrylamides of the present invention are likewise not shown nor suggested.

It has been reported in the literature that siloxane containing polymers provide good oxygen permeability, but otherwise lack wetting properties and the ability to absorb water. [See Y. J. Shur, et al., *J. Macromol*

Sci-Phys., B14, 565–572 (1977).] On the other hand, some polymers containing hydrophilic groups, such as poly(2-hydroxyethyl)methacrylate) ["poly(HEMA)"], poly(glyceryl methacrylate) ["poly(GMA)"] and poly(N,N-dimethylacrylamide) ["poly(DMA)" , can absorb water and have good wetting characteristics. The oxygen permeability of these water absorbable polymers depends upon the extent of hydration.

It is important to emphasize the significance of physical properties on lens performance. In order for a hydrogel to perform well as a contact lens, it must have enough "body", i.e. resilience, in the hydrated state to maintain a lens shape. At the same time, it must not be so rigid as to cause physiological problems. If the lens is too soft, it will drape and sag in such a way that it would be impossible to handle and also, the lens will deform too much in the eye, resulting in poor optics and poor visual acuity. If the lens is too rigid, it can cause physiological problems such as corneal staining, blanching, or even flattening of the cornea. Therefore, it is important to develop a develop a polymer with just the right resilience.

One factor directly affecting polymer resilience is the concentration of crosslinker. It is believed that a crosslinker, such as tetraethyleneglycol dimethacrylate ("TEGDMA"), randomly ties together long polymer chains, thus making the polymer network elastic. Polymer resilience is measured in terms of percent elongation. Based on polyHEMA, which has been accepted on the market for years and is used as a standard for contact lenses, a desirable percent elongation is 160–180%, while maintaining 2.5 to 3.0 g/mm² tear strength.

The present invention demonstrates that a hydrogel/siloxane material will provide strong, highly oxygen-permeable contact lenses which are not prone to coating. Essentially this is a hydrogel which does not depend solely on water for its oxygen permeability. Thus, it is possible to maintain high oxygen permeability without having high water content and the problems that normally accompany high water content lenses.

OBJECTS OF THE INVENTION

An object of the present invention is to provide new and useful hydrophilic siloxane-containing monomers for making contact lenses.

Another object of the invention is to prepare hydrogels from the monomers of the foregoing type which have moderate water contents (about 15–60%), but high oxygen permeabilities [greater than about Dk $25 \times 10^{-10}$ (Dk is measured in units of cm³(O₂)·cm/cm²·sec·cm Hg)].

A further object of the invention is to provide a contact lens having improved wettability, characterized by a receding contact angle of less than that of contact lenses made of polyMMA.

Still another object of the invention is to provide a hydrophilic siloxane copolymer, suitable for the fabrication of extended wear contact lenses, and having the following characteristics:
(1) moderate water content [about 15–60%];
(2) high oxygen permeability [Dk greater than about $25 \times 10^{-10}$];
(3) tear strength greater than about 1.0 g/mm²;
(4) percent elongation greater than or equal to about 80%;
(5) wettable, and
(6) minimal protein deposit formation.

SUMMARY OF THE INVENTION

A monomer is disclosed for making a contact lens with improved oxygen permeability and stability, such monomer having the following generalized structure:

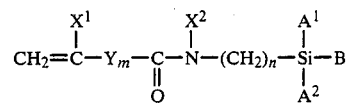

where: $X^1$ is $CH_3$ or H; $X^2$ is $CH_3$ or H; m is 0 or 1; n is an integer from 1 to 6; Y is selected from the group consisting of the following structures (the radical shown on the left of each formula being bonded to the carbon shown on the left of Y in the above structure):

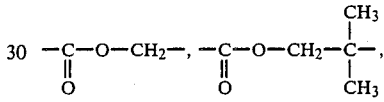

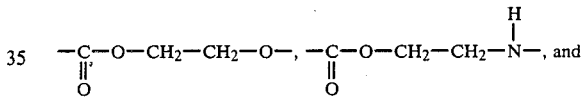

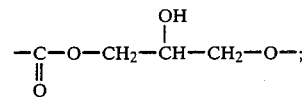

$A^1$ and $A^2$ are the same or different and are selected from lower alkyl and B groups; and B is a group of the structure:

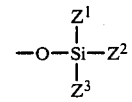

wherein $Z^1$, $Z^2$ and $Z^3$ are the same or different and are selected from the group including lower alkyl, phenyl, benzyl and tri-alkyl siloxy substituents.

A process is disclosed for making compounds of the above structural formula by: first, reacting an aminoalkyl trialkoxysilane with a hexa-alkyl disilazane to form a precursor; and second, reacting the precursor with an alkenoyl halide.

Two of the preferred siloxane-containing monomers of the present invention are N-[tris(trimethylsiloxy)silylpropyl]methacrylamide ("TSMAA") and N-[tris(trimethylsiloxy)silylpropyl]acrylamide ("TSAA").

A dimer or cross-linking agent is disclosed, having the following structure:

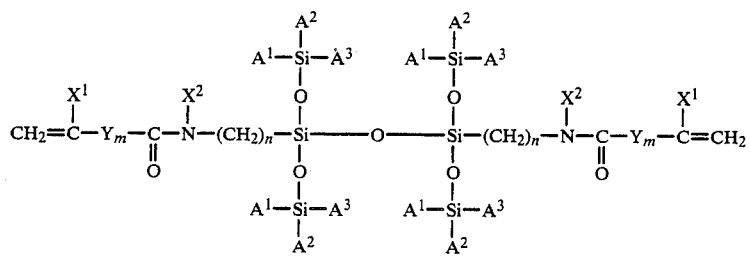

wherein: $X^1$ is $CH_3$ or H; $X^2$ is $CH_3$ or H; m is 0 or 1; n is an integer from 1 to 6; $A^1$ to $A^3$ are the same or different and are selected from lower alkyl, phenyl, benzyl and tri-substituted-siloxy; and Y is selected from the group consisting of the following structures (the radical shown on the left of each structure being bonded to a carbon bearing an X' substituent in the above structure):

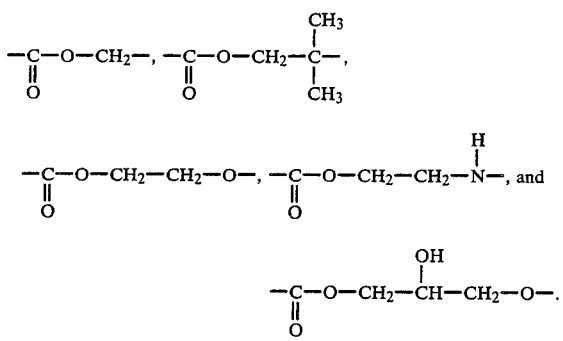

Various processes for preparing the monomers, dimers, polymers, copolymers and contact lenses therefrom are also disclosed.

DETAILED DESCRIPTION OF THE PREFERRED EMBODIMENTS

A monomer embodying the principles of the present invention is particularly suitable as a material for a contact lens, giving improved oxygen permeability and stability relative to prior siloxane-containing monomers. The monomer molecule has a first portion for increasing wettability and a second portion for increasing oxygen permeability as compared with presently existing contact lenses and the materials therefor.

The first portion is hydrophilic; it includes a side-chain functionality of the structural formula:

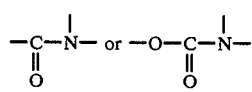

and has the general structure shown below in Formula I:

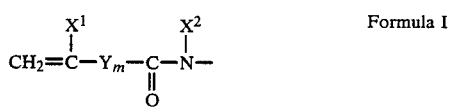

wherein $X^1$ is $CH_3$ or H; $X^2$ is $CH_3$ or H; m is 0 or 1; and Y is selected from the constituents shown in Table I. (The radical shown on the left of each constituent in Table I is to be bonded to the carbon atom shown on the left of Y in Formula I.)

TABLE I

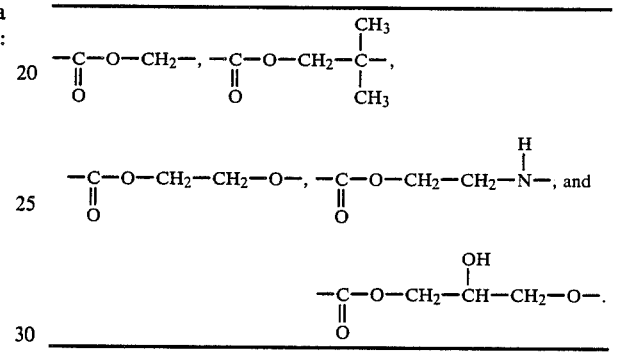

The second portion is hydrophobic in most embodiments of the present invention (some embodiments, however, can include hydrophilic substituents in this second portion); it includes a siloxane and has the general structure shown in Formula II:

Formula II wherein n is an integer from 1 to 6; $A^1$ and $A^2$ are the same or different and are selected from lower alkyl (i.e. $C_1$ to $C_6$) and B groups; and B is a group of the structure:

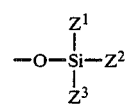

wherein $Z^1$, $Z^2$ and $Z^3$ are the same or different and are selected from the group including lower alkyl, phenyl, benzyl and tri-alkyl siloxy substituents.

Thus, a general structural formula for the monofunctional monomers of the invention is shown in Formula III, wherein the various substituents are as described above.

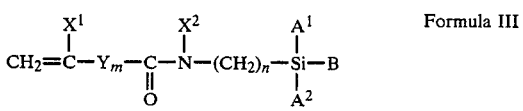

Formula III

The structures for presently preferred monomers of the present invention are shown below in Table II.

TABLE II
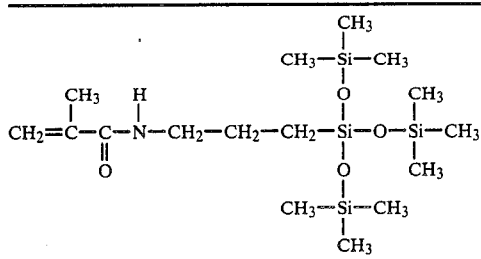
(TSMAA) N—[tris(trimethylsiloxy)silylpropyl]methacrylamide
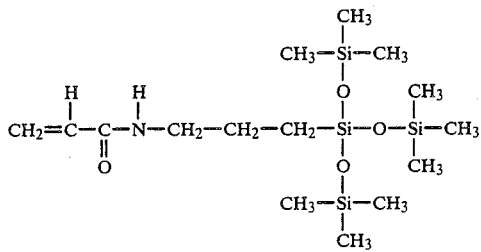
(TSAA) N—[tris(trimethylsiloxy)silylpropyl]acrylamide
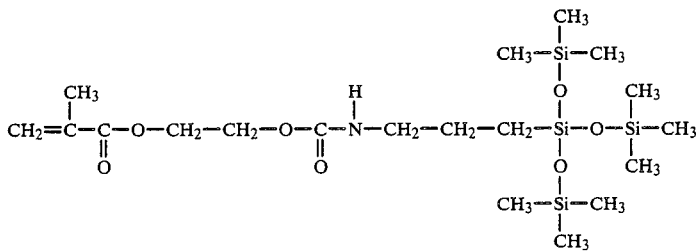
(TSMC) N—[tris(trimethylsiloxy)silylpropyl]methacryloxyethylcarbamate
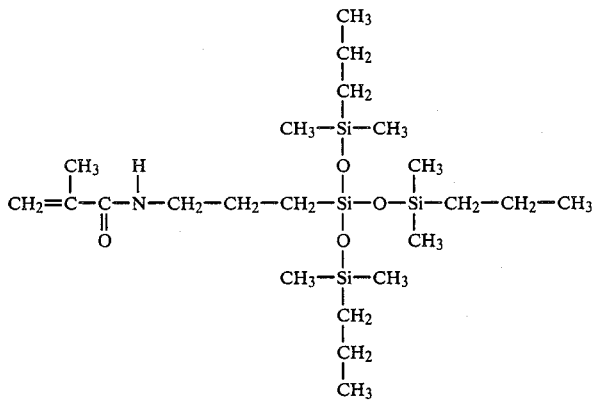
N—[tris(dimethylpropylsiloxy)silylpropyl]methacrylamide
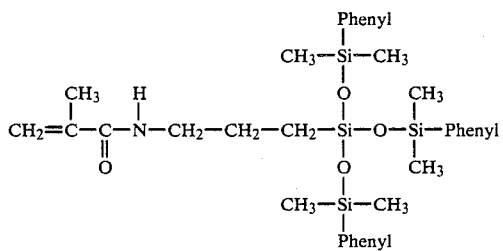
N—[tris(dimethylphenylsiloxy)silylpropyl]methacrylamide

TABLE II-continued

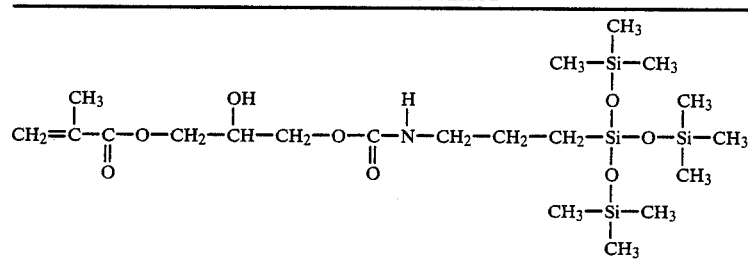

N—[tris(trimethylsiloxy)silylpropyl]methacryloxyglycerylcarbamate

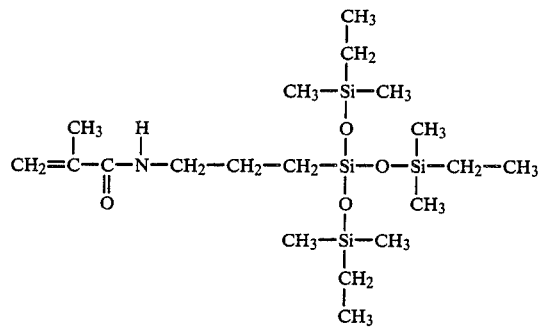

N—[tris(dimethylethylsiloxy)silylpropyl]methacrylamide

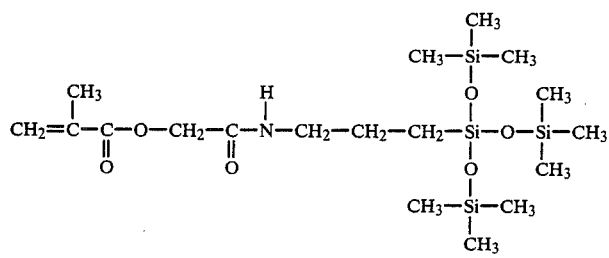

N—[tris(trimethylsiloxy)silylpropyl]methacryloxyacetamide

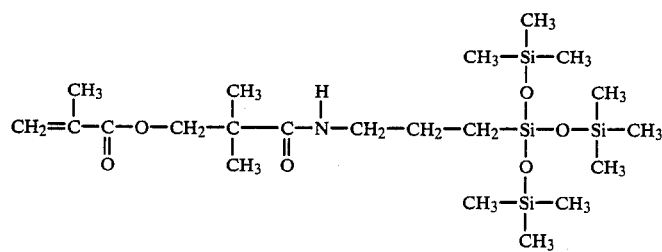

N—[tris(trimethylsiloxy)silylpropyl]methacryloxymethyl, dimethylacetamide

A dimer embodying the principles of the present invention is particularly suitable for use in formulating a contact lens material. A general structural formula for the dimer is shown below in Formula IV.

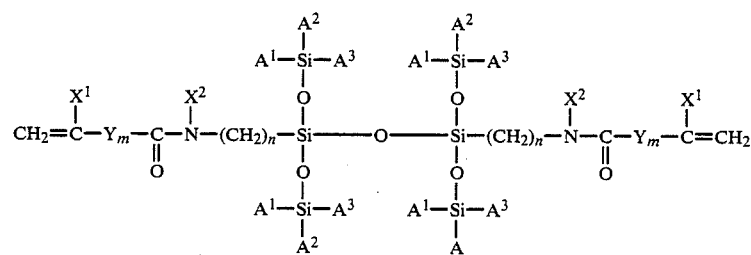

FORMULA IV wherein: $X^1$ is $CH_3$ or H; $X^2$ is $CH_3$ or H; m is 0 or 1; n is an integer from 1 to 6; $A^1$ to $A^3$ are the same or different and are selected from lower alkyl or B groups; and B is tri-substituted-siloxy; and Y is selected from the group consisting of the structures shown in Table I.

The structures for some presently preferred dimers, prepared in accordance with the present invention, are shown below in Table III.

MONOMER PREPARATION

The monomers of the present invention, as illustrated in Formula III are conveniently prepared as described generally in General Reaction Scheme A by initially condensing a substituted or unsubstituted alkenoyl halide with an amino alkyl silane. In General Reaction Scheme A: $X^1$ is $CH_3$ or H; $X^2$ is $CH_3$ or H; m is 0 or 1;

TABLE III

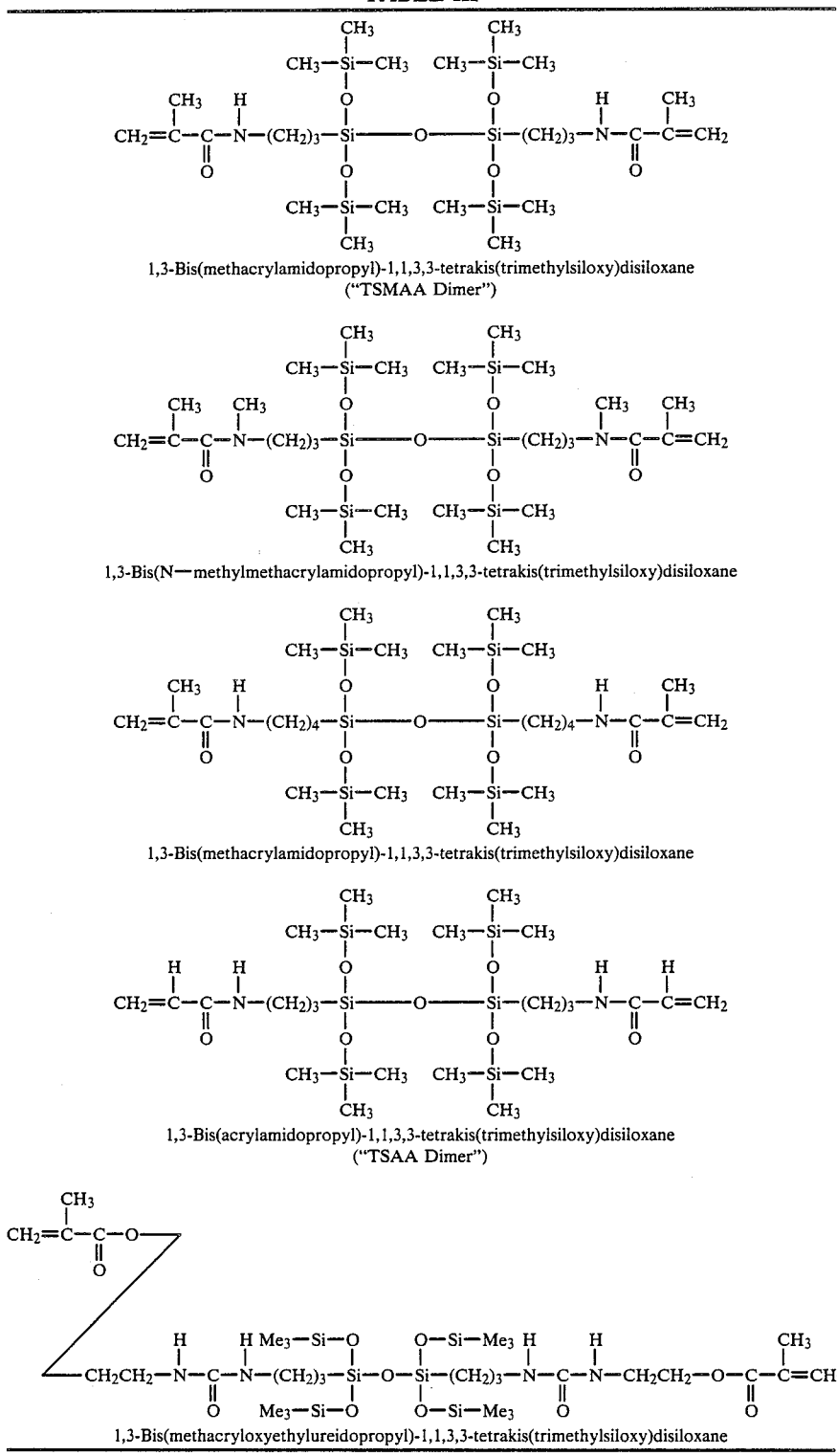

n is an integer from 1 to 6; Y is selected from Table I; $Z^1$, $Z^2$ and $Z^3$ are selected from lower alkyl or alkoxy or tri-substituted-siloxy; $A^1$ and $A^2$ are the same or different and are selected from lower alkyl or B groups; and B is tri-substituted-siloxy.

The condensation reaction typically is conducted in the presence of a suitable organic base, such as triethylamine, in an inert solvent, such as methylene chloride, and at a temperature below room temperature, typically about $-50°$ to $20°$ C. The alkenoyl halide typically is utilized in a slight molar excess relative to the amino alkyl silane to facilitate completion of the reaction. Suitable organic bases other than triethylamine include pyridine, N,N-dimethylaniline, and N-methylmorpholine. Inert solvents which can be utilized include halogenated hydrocarbons generally, such as methylene chloride, chloroform, 1,2-dichlorethane, chlorobenzene and mixtures thereof. Other suitable inert solvents are tetrahydrofuran, dioxane, hexane, benzene, and toluene.

GENERAL REACTION SCHEME A

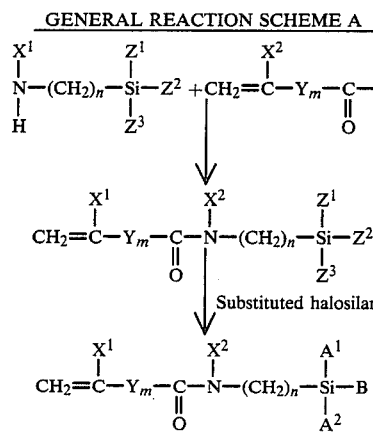

For purposes of this invention alkenoyl groups include methacryloyl and acryloly Alternatively, isocyanatoethyl methacrylate can be used instead of the alkenoyl halides. Halogen includes chlorine and bromine, with chlorine being presently preferred.

The aminoalkylsilanes include, for example: aminopropyl triethoxysilane, methylaminopropyl trimethoxysilane, 4-aminobutyl triethoxysilane, and 4-aminobutyl dimethyl methoxysilane. Many of the aminoalkylsilanes are available commercially and can be purchased from Petrach Systems, Inc., of Bristol, Pa. Typically, the silane is substituted with alkoxy groups, having 1-4 carbon atoms such as methoxy, ethoxy and the like.

After the condensation reaction has been completed, the desired siloxanes can be obtained by reacting the condensation products with appropriately substituted halosilanes. For example, when trimethylchlorosilane is allowed to react with N-(triethoxysilylpropyl)methacrlamide, there is obtained tris-(trimethylsiloxy)silylpropyl methacrylamide. These reactions are conducted in inert solvents such as those listed above at low temperatures, and typcially in the presence of water.

The substituted halosilanes may include, for example: trimethylchlorosilane, propyl dimethylchlorosilane, tri-n-propylchlorosilane, tri-i-propylchlorosilane, phenyl dimethylchlorosilane, benzyl dimethylchlorosilane, methyl dipropylchlorosilane, n-butyl dimethylchlorosilane, t-butyl dimethylchlorosilane, tri-fluoropropyl dimethylchlorosilane, and tris-trimethylsiloxy chlorosilane [prepared, for example, as taught in U.S. Pat. No. 4,216,303 (which also illustrates a preparation of a variety of tri-alkyl siloxy substituents)].

Alternatively, the interchange of groups on the silicon atom can be effected before the condensation reaction, as described in General Reaction Scheme B, by first, reacting an aminoalkyl alkoxysilane with a hexa-substituted disilazane to form a precursor (an aminoalkyl-disubstituted siloxane), and second, reacting the precursor with an alkenoyl halide, or an isocyanatoalkyl acrylate or methacrylate.

In General Reaction Scheme B: $X^1$ is $CH_3$ or H; $X^2$ is $CH_3$ or H; m is 0 or 1; n is an integer from 1 to 6; Y is selected from Table I; $Z^1$ to $Z^3$ are selected from lower alkyl or alkoxy or tri-substituted-siloxy, at least one being alkoxy; $Z^4$ to $Z^9$ are selected from lower alkyl or tri-substituted-siloxy; $A^1$ and $A^2$ are the same or different and are selected from lower alkyl or B groups; and B is tri-substituted-siloxy. The $A^1$, $A^2$ and B groups are derived from the $Z^4$ to $Z^9$ groups of the hexa-substituted disilazane.

GENERAL REACTION SCHEME B

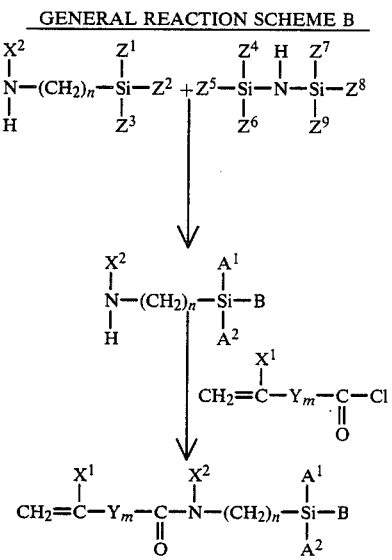

DIMER PREPARATION

The dimer or crosslinking agent of the present invention is prepared in accordance with General Reaction Scheme C.

In General Reaction Scheme C: $X^1$ is $CH_3$ or H; $X^2$ is $CH_3$ or H; m is 0 or 1; n is an integer from 1 to 6; Y is selected from Table I: $Z^1$ to $Z^3$ are selected from lower alkyl or alkoxy or tri-substituted-siloxy, at least one being alkoxy; $Z^4$ to $Z^9$ are selected from lower alkyl or tri-substituted-siloxy; and $A^1$ to $A^3$ are the same or different and are selected from lower alkyl and tri-substituted-siloxy. The A groups are derived from the $Z^4$ to $Z^9$ groups of the hexa-substituted disilizane.

An aminoalkylsiloxane is reacted with a hexa-substituted disilazane (e.g. hexamethyldisilazane) in the presence of water, and refluxed for about two days. An organic solvent, such as methylene chloride, is added to the organic product and the mixture is dried and then distilled; the dimer precursor being removed as a higher boiling distillation fraction. An organic solvent, such as methylene chloride, is added to the precursor, and the precursor is condensed with an excess of an alkenoyl halide to yield the dimer. The reactants described with reference to General Reaction Schemes A and B may typically be employed in this dimer synthesis. General Reaction Scheme A can also be employed to yield the dimer or crosslinking agent of the present invention, as a higher boiling by-product.

GENERAL REACTION SCHEME C

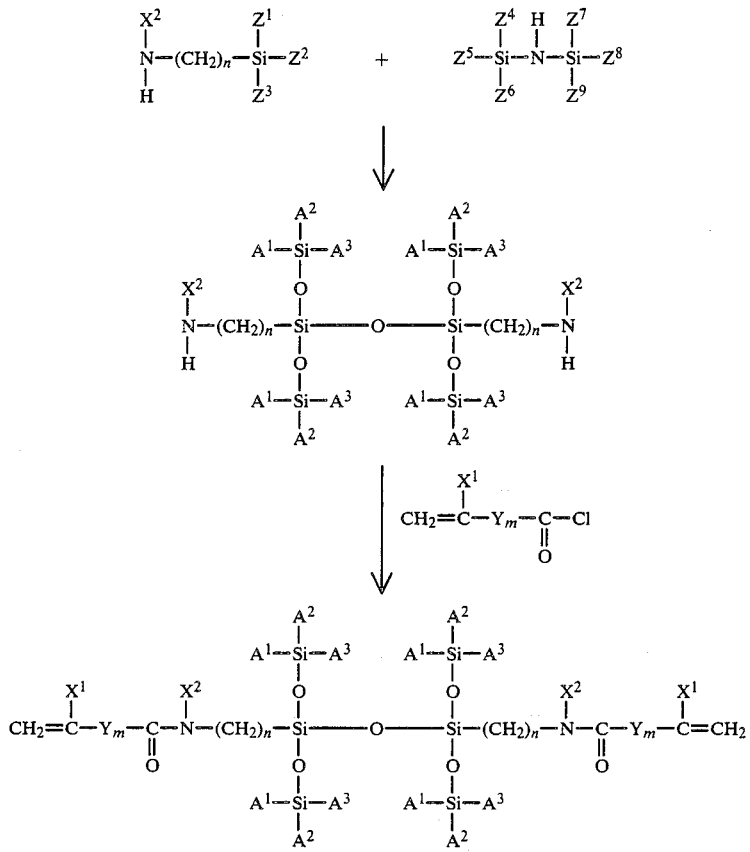

POLYMER AND COPOLYMER PEREPARATION

The monomers of the present invention may be polymerized alone or copolymerized with other monomers to give a contact lens material. A general formulation for the contact lens materials of the present invention is given below in Table IV, the component parts of which formulation are set forth in Tables V–VII; a presently preferred formulation is given in Table VIII.

TABLE IV

| Contact Lens Material Formulation | | |
|---|---|---|
| Component | | wt/wt % |
| (a) First Monomer | (See Formula III) | 30%–100% |
| (b) Second Monomer (plus) | (See Table V) | |
| (1) Optional 3rd Monomer | (See Table V) | 0%–70% |
| (c) Cross-linking Agent | (See Table VI) | 0%–10% |
| (d) Polymerization Initiator | (See Table VII) | 0%–5% |

TABLE V

| Presently Preferred Second and Third Monomers | |
|---|---|
| Methyl methacrylate | ("MMA") |
| Hydroxyethyl methacrylate | ("MEMA") |
| Glyceryl methacrylate | ("GMA") |
| N,N—dimethylacrylamide | ("DMA") |
| N—Vinyl pyrrolidone | ("NVP") |
| α-Methylglucoside-6-methacrylate | ("MGM") |
| Methacrylic acid | ("MAA") |

TABLE VI

Presently Preferred Crosslinkers

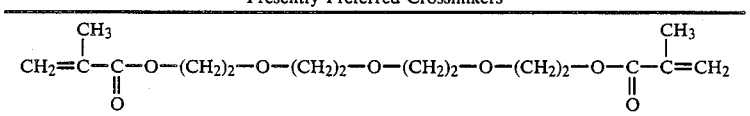

Tetraethyleneglycoldimethacrylate ("TEGDMA")

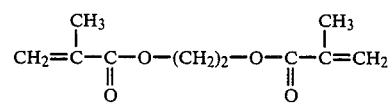

TABLE VI-continued

Presently Preferred Crosslinkers

Ethyleneglycoldimethacrylate ("EGDMA")

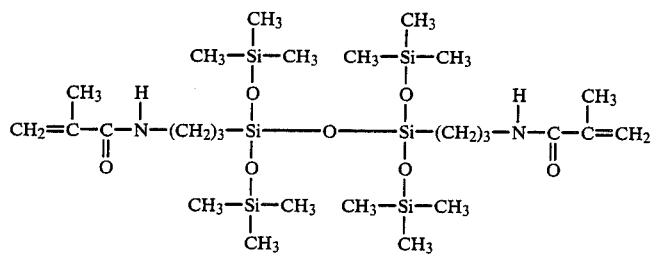

1,3-Bis(methacrylamidopropyl)-1,1,3,3-
tetrakis(trimethylsiloxy)disiloxane ("TSMAA Dimer")

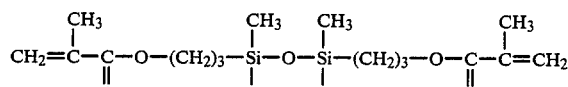

Bis(Methacryloxypropyl)tetramethyldisiloxane ("MADTMS Dimer")

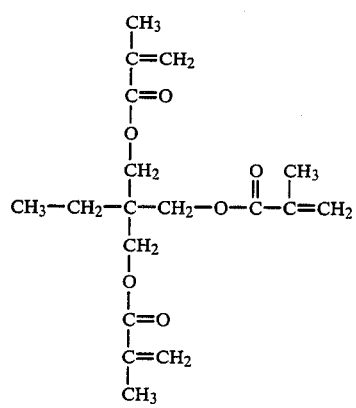

Trimethylolpropane trimethacrylate ("TMPTMA")

TABLE VII

Presently Preferred Polymerization Initiators

| | |
|---|---|
| Benzoin methyl ether | ("BME") |
| 2,2'-azobisisobutyronitrile | ("AIBN") |
| Isopropylperoxydicarbonate | ("IPP") |
| Methyl ethyl ketone peroxides | ("Lupersol DDM-9") |
| t-Butylperoxy pivalate | ("TBPP") |

Homopolymers of the present invention are prepared by combining a monomer having the general structural formula shown in Formula III (about 95–100 wt/wt%) with a polymerization initiator (or photoinitiator) such as those described in Table VII (about 0–5 wt/wt%). The mixture is dispensed into molds or slide cavities and irradiated with a sunlamp or medium pressure mercury lamp for 30–90 minutes, maintaining the temperature of the polymerizing mixture below about 35° C.

TABLE VIII

Presently Preferred Copolymer Formulation

| | | | |
|---|---|---|---|
| (a) First Monomer | (TSMAA) | 41.3 | wt % |
| (b) Second monomer | (DMA) | 48.6 | wt % |
| (c) Crosslinker | (TSMAA Dimer) | 5.6 | wt % |
| (d) Diluent | (MP)* | 4.0 | wt % |
| (e) Polymerization Initiator | (BME) | 0.4 | wt % |

*methyl pyrrolidone

Copolymers of the present invention are made by combining a first monomer having the general structural formula shown in Formula III (about 30–99 wt/wt%) with a second and/or third monomer, such as those described in Table V (about 0–70 wt/wt%) and a crosslinking agent, such as those described in Table VI, including dimers of the general structural formula shown in Formula IV (about 0–10 wt/wt%). A polymerization initiator (or photo-initiator) (about 0–5 wt/wt%) is added to the mixture.

The copolymers are prepared in the form of contact lenses using suitable lens molds, or in the form of films made between Teflon-lined glass slides, by first combining the components listed in Table IV. The comonomer mixtures are dispensed into molds or the slide cavities and then irradiated with a sunlamp or medium pressure mercury lamp for 30 to 90 minutes. The polymerizing mixtures were maintained below about 35° C.

EXAMPLES I–XXXVI

The following examples are given to enable those skilled in the art to more clearly understand and to practice the present invention. They should not be considered as a limitation on the scope of the invention, but merely as being illustrative and representative thereof.

EXAMPLE I

This Example and Reaction Scheme I illustrate a method for the synthesis of TSMAA, one of the preferred monomers of the present invention.

REACTION SCHEME I

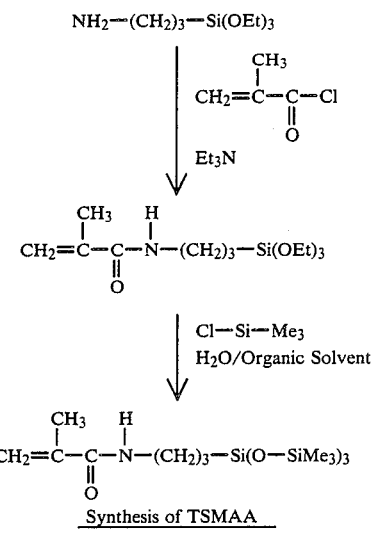

Synthesis of TSMAA

The intermediate methacrylamide shown in Reaction Scheme I was only crudely isolated in this preparation. Purification was done on the final product.

Freshly dried triethylamine (9.09 g, 0.09M) and methylene chloride (100 ml) were cooled to 0° C. 3-Aminopropyl triethoxysilane (10.0 g, 0.045M) was added to the methylene chloride solution. The methacryloyl chloride (7.1 g., 0.067M) was added dropwise. A white precipitate resulted. After 0.5 hours the reaction mixture was filtered and stripped on a rotary evaporator using an aspirator through a drying trap. The resultant viscous fluid was taken up in 20 ml of dry THF and filtered.

The THF solution and trimethylchlorosilane (29.5 g, 0.27M) were placed in separate dropping funnels. They were added simultaneously to 100 ml of 10% water in THF at 0°. After 0.5 hours the solution was neutralized to litmus using NaHCO$_3$. The material was filtered and dried.

The solvent, but not the silicone oil, was stripped on the rotary evaporator. The product (23.7 g) was dissolved in ethyl acetate (100 ml) and washed for 15 minutes with aqueous ammonia (50 ml). It was washed with 10% citric acid (50 ml) and distilled water (50 ml). The ethyl acetate solution was dried and filtered. The crude product (20.2 g, 53%) was recovered by stripping on the rotary evaporator. The crude product was distilled under vacuum (146° at 0.7 mm Hg) using 1% of an inhibitor. The clear product (4.70 g, 93% purity) contained no diester and about 4.0% low boilers which could be removed in a larger distillation.

The resulting monomer had the following analytical characteristics:

$^1$H NMR δ: 6.03 (s, 1, C—NH—C); 5.61 (s, 1, C=CH$_2$); 5.24 (s, 1, C=CH$_2$); 3.29, 3.22, 3.15, 3.05 (q, 2, N—CH$_2$—C); 1.86 (s, 3, C=C(CH$_3$)—CO—N—); 1.64, 1.56, 1.47, 1.39 (q, 2, C—CH$_2$—C); 0.46 center (q, 2, C—CH$_2$Si—(OSiMe$_3$)$_3$); 0.049 (s, 27, O—Si—Me$_3$).

$^{13}$C NMR δ: 168.5 (—C=O); 140.5 (=C); 118.9 (H$_2$C=); 42.1 (—NH—CH$_2$—); 23.6 (—CH$_2$—); 18.7 (—CH$_3$); 11.7 (—CH$_2$—Si—(OSiMe$_3$)$_3$); 1.7 (Si—(OSiMe$_3$)$_3$).

$^{29}$Si NMR δ: 7.95 (3Si, (OSiMe$_3$); −66.1 (1Si, —(CH$_2$Si—(OSiMe$_3$)$_3$)).

IR 3350 (N—H str); 1665 (O=C(N)C str); 1640 (H$_2$C=C str); 1050 (SiOSi str); 840 (OSiMe$_3$ str); 752 (OSiMe$_3$ str).

bp 146° C. (0.7 mm Hg).

EXAMPLE II

A presently preferred synthetic route for synthesis of TSMAA is shown in Reaction Scheme II. A wide variety of conditions for accomplishing the first step of Reaction Scheme II were investigated (see Table IX).

(1) Preparation of tris(trimethylsiloxy)silylpropylamine

Aminopropyltriethoxysilane (200 ml, 0.84M) and hexamethyldisilazane (1000 ml, 4.76M) were combined. Dibutyltin dilaurate (10 ml) was added. Distilled water (1000 ml, 55.5M) was added and an exotherm occurred. The mixture was allowed to stir overnight. The reaction mixture forms a very stable emulsion which was broken by the addition of sodium chloride, and the lower aqueous phase was discarded. The upper organic phase was washed twice with brine (500 ml). The organic phase was dried over molecular sieves, filtered and stripped on the rotary evaporator to yield a colorless liquid (223 g, 75.2%). The crude product was distilled to give the pure product (58% of pot charge). The boiling point was 79° C. at 0.30 mm Hg.

The product had the following characteristics:

$^1$H NMR δ: 2.6 (t, 2, H$_2$N—CH$_2$—); 1.4 (m, 2, CH$_2$CH$_2$CH$_2$); 1.1 (s, 2, NH$_2$); 0.31 (t, 2, —CH$_2$—Si); 0.03 (s, 27, —OSiMe$_3$).

$^{13}$C NMR δ: 45.1 (H$_2$N—CH$_2$); 27.8 (—CH$_2$CH$_2$—CH$_2$); 11.4 (CH$_2$—Si); 1.7 (OSiMe$_3$).

$^{29}$Si NMR δ: 7.4 (4Si, C—Si—(OSiMe$_3$); 65.6 (1Si, Si—OSiMe$_3$).

REACTION SCHEME II

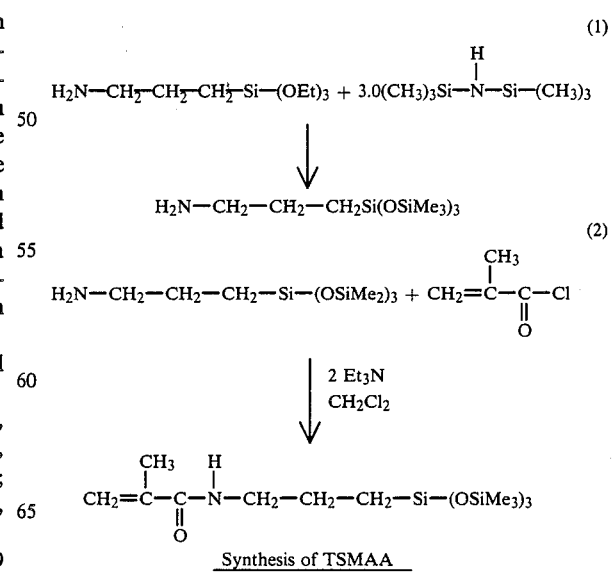

Synthesis of TSMAA

TABLE IX

Comparison of Reaction Conditions for Reaction of
Aminopropyltriethoxysilane (A) with Mexamethyldisilizane (B)

| Mole Ratio (A):(B) | Product vs.[1] Starting Material | % Dimer | Reaction Conditions | Catalyst[2] | Overall Yield of Monomer after Distillation |
|---|---|---|---|---|---|
| 1:3  | 50.2%  | 21.7% | Room temp. 3 days | TBT   | *     |
| 1:4  | 53.3%  | 19.0% | Room temp. 4 days | TBT   | *     |
| 1:6  | 52.0%  | 11.2% | Room temp. 3 days | TBT   | *     |
| 1:12 | 42.0%  | 12.0% | Room temp. 1 day  | BSLO  | 29.9% |
| 1:6  | 63.3%  | 19.6% | Reflux 5.5 hours  | TBT   | *     |
| 1:6  | 47.2%  | 15.7% | Reflux 22 hours   | TBT   | *     |
| 1:3  | 54.6%  | 19.7% | Reflux 5 hours    | TBT   | *     |
| 1:4  | 79.3%  | 23.7% | Reflux 5 hours    | TBT   | 31.2% |
| 1:4  | 58.2%  | 23.1% | Reflux 5 hours    | TBT   | 23.3% |
| 1:4  | 95.1%  | 20.1% | Reflux 6 days     | None  | *     |
| 1:4  | 78.7%  | 26.5% | Reflux 2 days     | None  | 41.1% |
| 1:6  | 96.8%  | 20.2% | Reflux 2 days     | None  | 46.8% |
| 1:6  | 103.1% | 15.1% | Reflux 3 days     | None  | 40.2% |

[1]G.C. ratio of product to original amount of starting material
[2]BSL = Dibutyltin dilaurate
TBT = Tetrabutyl titanate
Overall yield not determined; relative amounts identified by G.C.

Several catalysts were alternatively utilized. Dibutyltin dilaurate, stannous octoate and tetrabutyl titanate all gave similar results for catalysis of the reaction. Tetrabutyl titanate was the preferred catalyst since it was easiest to remove during the workup. Tetrabutyl titanate converts to insoluble titanium dioxide very rapidly in the presence of water and may be easily removed by filtration.

Non-catalyzed reactions were also conducted. These uncatalyzed reactions had higher yields (average=42.7%) from the distillation than did the catalyzed reactions (average=28.1%).

(2) Preparation of TSMAA

Distilled tris(trimethylsiloxy)silylpropylamine (5.0 g, 0.014M) was combined with dry pyridine (2.2 ml, 0.28M) and methylene chloride (25 ml). Distilled methacryloyl chloride (1.48 ml, 0.015M) was added slowly. After stirring for 2 hours, the reaction mixture was poured into water (25 ml). The organic phase was washed with 25 ml each of aqueous ammonia, 10% citric acid, twice with saturated sodium bicarbonate and water. The organic phase was dried over molecular sieves. It was filtered and stripped on the rotary evaporator. The resulting product (5.4 g, 91.6%) was identical to the material prepared in Example I.

This alternative synthesis of TSMAA (Scheme II) produces predominantly the desired product, without need for distillation.

EXAMPLE III

Tris(trimethylsiloxy)silylpropyl acrylamide (TSAA) was prepared by Reaction Scheme III. This synthetic method results in TSAA which does not require distillation to remove dimers.

The starting material [tris(trimethylsiloxy)silylpropylamine] was prepared using the methods described in step (1) of Example II.

REACTION SCHEME III

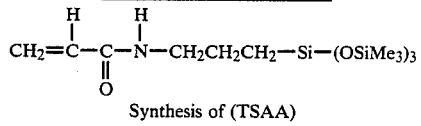

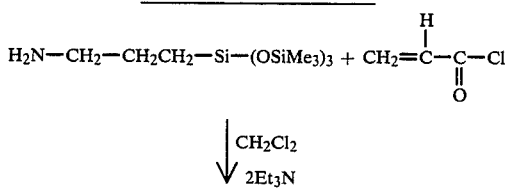

-continued
REACTION SCHEME III $$CH_2=C-C-N-CH_2CH_2CH_2-Si-(OSiMe_3)_3$$

Synthesis of (TSAA)

Tris(trimethylsiloxy)silylpropylamine (75 g, 0.21M) was combined with triethylamine (45 ml, 0.42M) and dry methylene chloride (500 ml). The solution was cooled to 10° C. using an ice bath. Acryloyl chloride (18.5 ml, 0.22M) was added very slowly. The mixture was stirred for three hours. It was filtered and the filter cake was washed with methylene chloride.

The solution was washed with (250 ml each) water, aqueous ammonia, and water. It was dried over molecular sieves (3A). The solution was filtered through Whatman #5 paper.

Copper (I) chloride, phenothiazine, and p-methoxyphenol (MeHQ) were added as inhibitors. The solvents were stripped off on the rotary evaporator. Green crystals (85.3 g, 99.8%) were recovered. The purity by gas chromatography was 94.5% with two high boiling impurities at 3.0% and 1.5%. The crude TSAA was purified by vacuum distillation. Crystals (52.25 g, 61.1%) formed after the material cooled. The purity was 97.5% by gas chromatography. No dimer was detected.

NMR data was obtained on a sample without a TMS reference. $^1H$ shift values were calculated from the CHCl$_3$ impurity peak in CDCl$_3$ at 7.26 δ; $^{13}C$ spectral assignments were based on the central peak of CDCl$_3$ at 77.06 δ. The $^{29}Si$ spectrum had no reference, only relative positions of the two peaks are reported. The resulting monomer had the following characteristics:

$^1H$ NMR δ: 6.2-5.5 (m, 4.2, —NH—CO—CH=CH$_2$); 3.3 (q, 2.1, N—CH$_2$—); 1.6 (m, 2.2, —CH$_2$—); 0.55 (m, 2.2, —CH—Si); 0.09 (s, 24.9, O—SiMe$_3$)

$^{13}C$ NMR δ: 168 (C=O); 131.1 (=CH); 126.1 (=CH$_2$); 42.1 (N—CH$_2$); 23.6 (—CH$_2$); 11.7 (—CH$_2$—Si); 1.79 (—O—SiMe$_3$).

$^{29}Si$ NMR δ: 0.0 (Si—(OSiMe$_3$)$_3$); −74.1 (C—Si—(OSiMe$_3$)$_3$).

bp 143° C. (0.6 mm Hg).
mp 48.5°-50° C.

EXAMPLE IV

The following example and Reaction Scheme IV illustrate the synthesis of tris(trimethylsiloxy)silylpropyl methacryloxyethyl carbamate (TSMC).

(1) Synthesis of N-(Triethoxysilylpropyl)methacryloxyethylcarbamate

3-Isocyanatopropyltriethoxy silane was purified by vacuum distillation, and a material of greater than 95% purity was obtained. To 4.95 g (0.02 moles) of the distilled isocyanatopropyl triethoxysilane was added 2.34 g (0.02 moles) of hydroxyethylmethacrylate and 0.02 g ($3.17 \times 20^{-5}$ moles) of dibutyltindilaurate.

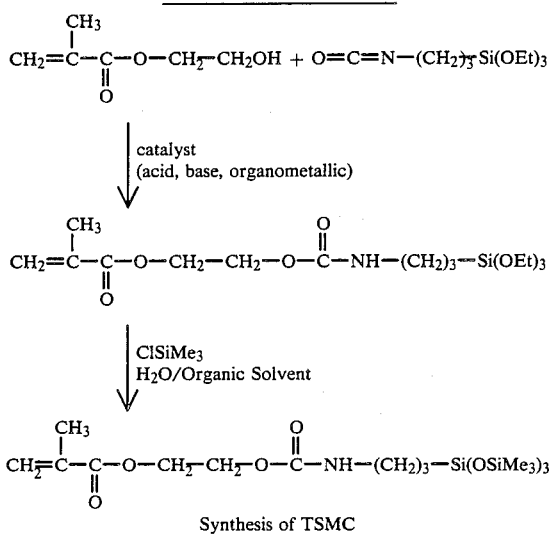

REACTION SCHEME IV

Synthesis of TSMC

The reaction mixture was stirred at room temperature for two hours, and yielded product having the following characteristics:

$^1$H NMR δ: 6.13 (d, 1, C=CH$_2$); 5.59 (s, 1, C—CH$_2$); 5.57 (m, 1, NH); 4.32 (d, 4, OCH$_2$CH$_2$); 3.94–3.70 (m, 6, CH$_3$CH$_2$); 3.21–3.07 (m, 2, CH$_2$CH$_2$CH$_2$); 1.95 (s, 3, CH$_3$C=C); 1.72–1.54 (m, 2, SiCH$_2$); 1.22 (t, 3, CH$_3$CH$_2$); 0.72–0.04 (m, 2, NCH$_2$CH$_2$).

$^{13}$C NMR δ: 167.13 (C=O); 156.19 (NHC=O); 136.09 (=C); 125.87 (H$_2$C=O); 63.00 (OCH$_2$CH$_2$); 62.41 (OCH$_2$CH$_2$); 58.45 (OCH$_2$CH$_3$); 43.50 (CH$_2$N); 23.30 (CH$_2$CH$_2$CH$_2$); 18.26 (CH$_2$Si); 7.69 (CH$_2$CH$_3$).

$^{29}$Si NMR δ: −45.75.

Synthesis of Tris(trimethylsiloxy)silylpropylmethacryloxyethyl carbamate (TSMC)

To a solution of one gram of distilled water and 9 grams of tetrahydrofuran (THF), which was kept at 0° C. by an ice bath, was added by dropping funnel, simultaneously, a 50% solution of trimethylchlorosilane in THF and a 50% THF solution of triethoxysilylpropyl methacryloxyethylcarbamate. The reaction was stirred at 5°–10° C. for 2 hours, followed by 24 hours at room temperature (about 24° C.). The reaction mixture was worked up by neutralizing the upper layer with a saturated sodium bicarbonate wash, followed by drying over molecular sieves and stripping of solvent by vacuum on a rotoevaporator with a bath temperature of 50° C. This yielded 0.97 g of TSMC (68% theoretical).

EXAMPLE V

TSMAA Dimer Precursor Synthesis (Reaction Scheme V)

As in Example II, aminopropyltriethoxysilane (100 g, 0.45M) was combined with hexamethyldisilazane (217 g, 1.35M). Water (480 ml, 26.6M) was added. The mixture was stirred and refluxed for two days. After the two days of reflux, two phases separated easily. The lower, aqueous phase was discarded.

Methylene chloride (500 ml) was added to the organic phase. The methylene chloride solution was dried over molecular sieves (3A). It was filtered through Whatman #5 paper. The solvent and hexamethyldisiloxane were stripped off on the rotary evaporator. A water white, clear fluid (105.6 g, 66.5%) was recovered.

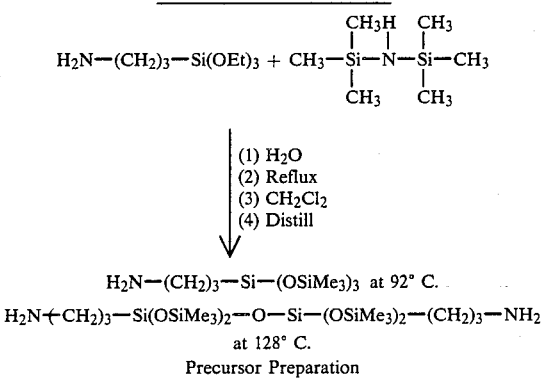

REACTION SCHEME V

Precursor Preparation

The material was purified by vacuum distillation through a vigreux column. The monomer precursor fraction was removed at 92° C. The dimer precursor fraction was removed at 128° C. The conditions and yields are shown in Table X.

The overall yield after distillation was 46.8%. The tris(trimethylsiloxy)silylpropylamine (monomer precursor) was 96.2% pure by gas chromatography. Further characterization was not done. The 1,3-bis(aminopropyl)-1,1,3,3-tetrakis(trimethylsiloxy)disiloxane (dimer precursor) was 86.5% pure by gas chromatography. The $^1$H, $^{13}$C and $^{29}$Si NMR of the dimer precursor are described below: $^1$H NMR δ: 2.60 (t, 4, N—CH$_2$—); 1.43 (m, 4, C—CH$_2$—C); 1.19 (s, 4, H$_2$N—C); 0.50 (m, 4, C—CH$_2$—Si); 0.046 (s, 35, Si—(OSiMe$_3$)$_2$).

$^{13}$C NMR δ: 45.2 (H$_2$N—CH$_2$—C); 27.79 (CH$_2$—CH$_2$—CH$_2$); 11.48 (C—CH$_2$—Si); 1.78 (Si—(OSiMe$_3$)$_2$).

$^{29}$Si NMR δ: 7.69 (Si—(OSiMe$_3$)$_2$); −67.4 [C—Si—(OSiMe$_3$)$_2$—O—Si(OSiMe$_3$)$_2$—C].

TABLE X

Conditions for Distillation of Tris(trimethylsiloxy)silylpropylamine

| Identity | B.P. | Vacuum (mm Mg) | Grams Recovered |
| --- | --- | --- | --- |
| Monomer precursor | 92° C. | 1.0 | 74.4 g |
| Dimer precursor | 128° C. | 1.0 | 15.6 g |

EXAMPLE VI

Synthesis of 1,3-Bis(methacrylamidopropyl)1,1,3,3-tetrakis(trimethylsiloxy)disiloxane As illustrated in Reaction Scheme VI, TSMAA dimer precursor of Example V (39.5 g, 0.073M) was combined with triethylamine (30 ml, 0.29M) and methylene chloride 250 ml). Methacryloyl chloride (1.95 ml, 0.16M) was added slowly. The mixture was stirred for one hour and then filtered. The filter cake was washed with methylene chloride.

The methylene chloride solution was washed with water, aqueous ammonia, and water (150 ml each). It was dried over molecular sieves (3A). The solution was filtered through Whatman #5 paper. The solvents were stripped off on the rotary evaporator. Light yellow crystals (43.5 g, 87.6%) were recovered. The TSMAA dimer was 68.6% pure by gas chromatography.

The crude TSMAA dimer was purified by column chromatography using 95% methylene chloride/5% acetonitrile on silica gel 60 (230–400 mesh). The fractions containing pure dimer were combined. The solvent was stripped off on the rotary evaporator. White crystals (20.6 g; 41.5%) (m.p.=79°–80° C.) were recovered; 98% pure by GC. The TSMAA dimer NMR data follows:

$^1$H NMR δ: 6.1 (broad, 1.2, —NH—C=O); 5.63 (s, 1.7, =CH$_2$); 3.27 (q, 4.0, N—CH$_2$); 1.92 (s, 6.0, CH$_2$=C(CH$_3$)—CH$_2$); 1.55 (m, 4, C—CH$_2$—C); 0.55 (m, 4, —CH$_2$—Si); 0.068 (s, 36, O—SiMe$_3$).

$^{13}$C NMR δ: 168.4 (C=O); 140.4 (=C); 118.9 (=CH$_2$); 42.3 (N—CH$_2$—); 23.5 (C—CH$_2$—C); 18.7 (CH$_2$=C(CH$_3$)—CH$_3$); 11.7 (—CH$_2$—Si); 1.8 (O—Si—Me$_3$).

$^{29}$Si NMR δ: 0.0* (4.17 Si,OSiMe$_3$); —76.2** (1.83 Si, (Si—(OSiMe$_3$)$_2$).

*Set as reference point (shift relative to TMS not known)
**Shift relative to OSiMe$_3$

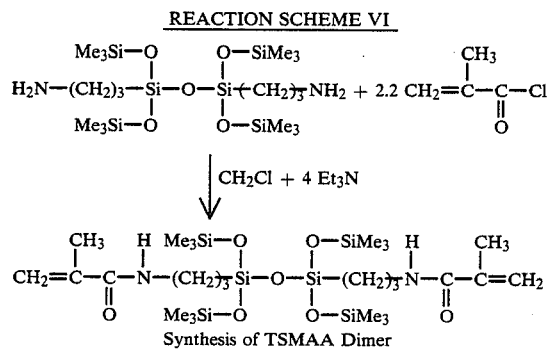

Synthesis of TSMAA Dimer

EXAMPLE VII

By substituting an equivalent quantity of methylaminopropyl trimethoxysilane for aminopropyl triethoxysilane in Example I and otherwise following the procedures of Example I, there is obtained N-methyl-N-[tris(trimethylsiloxy)silylpropyl]methacrylamide.

EXAMPLE VIII

By substituting an equivalent quantity of 3-aminobutyl triethoxysilane for aminopropyl triethoxysilane in Example I and otherwise following the procedures of Example I, there is obtained N-[tris(trimethylsiloxy)silylbutyl]methacrylamide.

EXAMPLE IX

By substituting an equivalent quantity of propyl dimethylchlorosilane for trimethylchlorosilane in Example I and otherwise following the procedures of Example I, there is obtained N-[tris(propyldimethylsiloxy)silylpropyl]methacrylamide.

EXAMPLE X

By substituting an equivalent quantity, in equal amounts, of propyl dimethylchlorosilane and trimethylchlorosilane for the trimethylchlorosilane in Example I and otherwise following the procedures of Example I, there is obtained a mixture of N-[(propyldimethylsiloxy)-bis-(trimethylsiloxy)silylpropyl]methacrylamide and N-[(trimethylsiloxy)-bis-(propyldimethylsiloxy)silylpropyl]methacrylamide.

EXAMPLE XI

By substituting an equivalent quantity of 4-aminobutyl dimethyl methoxysilane for 3-aminopropyl triethoxysilane in Example I and otherwise following the procedures of Example I, there is obtained N-[bis(methyl)(trimethylsiloxy)silylbutyl]methacrylamide.

EXAMPLE XII

By substituting an equivalent quantity of isocyanatoethyl methacrylate for methacryloyl chloride in Example II and otherwise following the procedures of Example II, there is obtained N-[tris(trimethylsiloxy)silylpropyl]ethylureidomethacrylate.

EXAMPLE XIII

By substituting an equivalent quantity of tri(n-propyl)chlorosilane for trimethylchlorosilane in Example I and otherwise following the procedures of Example I, there is obtained N-[tris(tri-n-propylsiloxy)silylpropyl]methacrylamide.

EXAMPLE XIV

By substituting an equivalent quantity of tri(i-propyl)chlorosilane for trimethylchlorosilane in Example I and otherwise following the procedures of Example I, there is obtained N-[tris(tri-i-propylsiloxy)silylpropyl]methacrylamide.

EXAMPLE XV

By substituting an equivalent quantity of phenyl dimethylchlorosilane for trimethylchlorosilane in Example I and otherwise following the procedures of Example I, there is obtained N-[tris(phenyldimethylsiloxy)silylpropyl]methacrylamide.

EXAMPLE XVI

By substituting an equivalent quantity of benzyldimethylchlorosilane for trimethylchlorosilane in Example I and otherwise following the procedures of Example I, there is obtained N-[tris(benzyldimethylsiloxy)silylpropyl]methacrylamide.

EXAMPLE XVII

By substituting an equivalent quantity of methyl dipropylchlorosilane for trimethylchlorosilane in Example I and otherwise following the procedures of Example I, there is obtained N-[tris(methyldipropylsiloxy)silylpropyl]methacrylamide.

EXAMPLE XVIII

By substituting an equivalent quantity of n-butyl dimethylchlorosilane for trimethylchlorosilane in Example I and otherwise following the procedures of Example I, there is obtained N-[tris(n-butyldimethylsiloxy)silylpropyl]methacrylamide.

EXAMPLE XIX

By substituting an equivalent quantity of t-butyl dimethylchlorosilane for trimethylchlorosilane in Example I and otherwise following the procedures of Example I, there is obtained N-[tris(t-butyldimethylsiloxy)silylpropyl]methacrylamide.

EXAMPLE XX

By substituting an equivalent quantity of tri-fluoropropyl dimethylchlorosilane for trimethylchlorosilane in Example I and otherwise following the procedures of Example I, there is obtained N-[tris(tri-fluoropropyl-dimethylsiloxy)silylpropyl]methacrylamide.

EXAMPLE XXI

By substituting an equivalent quantity of tris-trimethylsiloxy chlorosilane for trimethylchlorosilane in Example I and otherwise following the procedures of Example I, there is obtained N-[tris(tris-trimethylsiloxysiloxanyl)silylpropyl]methacrylamide.

EXAMPLE XXII

By substituting an equivalent quantity of methylaminopropyl trimethoxysilane for aminopropyl triethoxysilane in Example V and otherwise following the procedures of Example V, there is obtained 1,3-bis(N-methylaminopropyl)-1,1,3,3-tetrakis(trimethylsiloxy)-disiloxane, a dimer precursor.

EXAMPLE XXIII

By substituting an equivalent quantity of 3-aminobutyl triethoxysilane for aminopropyl triethoxysilane in Example V and otherwise following the procedures of Example V, there is obtained 1,3-bis(aminobutyl)-1,1,3,3-tetrakis(trimethylsiloxy)disiloxane, a dimer precursor.

EXAMPLE XXIV

By substituting an equivalent quantity of acryloyl chloride for methacryloyl chloride in Example VI and otherwise following the procedures of Example VI, there is obtained 1,3-Bis(acrylamidopropyl)-1,1,3,3-tetrakis(trimethylsiloxy)disiloxane.

EXAMPLE XXV

By substituting an equivalent quantity of isocyanatoethyl methacrylate for methacryloyl chloride in Example VI and otherwise following the procedures of Example VI, there is obtained 1,3-Bis(methacryloxyethylureidopropyl)-1,1,3,3-tetrakis(trimethylsiloxy)-disiloxane.

EXAMPLE XXVI

A series of copolymers were prepared according to the present invention, varying the mole ratio of the DMA and TSMAA comonomers that were used. Physical properties of the hydrated copolymers were measured using standard procedures; the results are described in Table XI. The results indicate that tear strength decreases and hydration increases as the DMA concentration increases. Modulus decreases as DMA concentration increases, until the DMA/TSMAA mole ratio reaches about 5/1, and then the modulus rises with continued increase in DMA concentration.

EXAMPLE XXVII

A series of copolymers were prepared according to the present invention, varying the cross-linker used and its concentration. Physical properties of the copolymers are described in Table XII. The TSMAA Dimer cross-linker (one of the dimers of the present invention) gave higher modulus and tear strength than did TEGDMA at a similar molar concentration, while the other physical properties were comparable. Bis(methacryloxypropyl)tetramethyldisiloxane (MAPTMS Dimer) also gave better properties than TEGDMA. Ethylene glycol dimethacrylate (EGDMA) and trimethylolpropanetrimethacrylate (TMPTMA) were also tested, but were found to be not as effective as the TSMAA Dimer.

TABLE XI

Physical Properties Of DMA/TSMAA Copolymers

| Sample | Wt. % Formulation | Mole Ratio DMA:TSMAA | % Conversion | Modulus ($\times 10^{-6}$ dynes/cm$^2$) | $O_2$ ($\times 10^{10}$ Dk)* | % Hydration |
|---|---|---|---|---|---|---|
| A | DMA 39.21<br>TSMAA 55.32<br>TEGDMA 1.01<br>BME 0.41<br>MP 4.04 | 3.0:1 | DMA > 99<br>TSMAA 96.8 | 2.6 ± 0.8 | 58 | 37.6 ± 0.4 |
| B | DMA 42.76<br>TSMAA 51.81<br>TEGDMA 1.04<br>BME 0.40<br>MP 3.98 | 3.5:1 | DMA > 99<br>TSMAA 97.1 | 3.2 ± 0.2 | 43 | 37.9 ± 2.6 |
| C | DMA 45.80<br>TSMAA 48.59<br>TEGDMA 1.03<br>BME 0.41<br>MP 4.03 | 4.0:1 | DMA > 99<br>TSMAA 98.2 | 2.6 ± 0.4 | 51 | 42.1 ± 0.8 |
| D | DMA 47.16<br>TSMAA 47.40<br>TEGDMA 0.99<br>BME 0.40<br>MP 4.06 | 4.23:1 | DMA > 99<br>TSMAA 97.5 | 2.0 ± 0.3 | 47 | 42.6 – 44.2 |
| E | DMA 48.57<br>TSMAA 45.89<br>TEGDMA 1.02<br>BME 0.40 | 4.5:1 | DMA > 99<br>TSMAA 96.9 | 1.8 ± 0.4 | 40 | 43.8 – 46.6 |

TABLE XI-continued

Physical Properties Of DMA/TSMAA Copolymers

| Sample | Wt. % Formulation | Mole Ratio DMA:TSMAA | % Conversion | Modulus ($\times 10^{-6}$ dynes/cm$^2$) | $O_2$ ($\times 10^{10}$ Dk)* | % Hydration |
|---|---|---|---|---|---|---|
| F | MP 4.11<br>DMA 49.59<br>TSMAA 44.87<br>TEGDMA 1.03<br>BME 0.40 | 4.7:1 | DMA > 99<br>TSMAA 96.8 | 1.8 ± 0.2 | 42 | 46.9 — 48.3 |
| G | MP 4.11<br>DMA 51.22<br>TSMAA 43.38<br>TEGDMA 0.88<br>BME 0.41 | 5.0:1 | DMA > 99<br>TSMAA 97.9 | 1.6 ± 0.1 | 43 | 50.3 ± 0.3 |
| H | MP 4.01<br>DMA 53.37<br>TSMAA 41.19<br>TEGDMA 1.01<br>BME 0.40 | 5.5:1 | DMA > 99<br>TSMAA 97.2 | 3.7 ± 0.9 | 33 | 50.6 ± 1.1 |
| I | MP 4.03<br>DMA 55.18<br>TSMAA 39.32<br>TEGDMA 1.00<br>BME 0.40<br>MP 4.10 | 6.0:1 | DMA > 99<br>TSMAA 97.4 | 3.8 ± 0.3 | 33 | 52.7 ± 0.4 |

*Dk unit = cm$^3$(O$_2$) · cm/cm$^2$ · sec · cm Hg

TABLE XII

Physical Properties of 5/1 MOLE RATIO DMA/TSMAA Copolymers With Changes In Crosslinker Concentration

| Sample | Wt. % Formulation | Mole % X-LINKER | Modulus ($\times 10^{-6}$ dynes/cm$^2$) | % Elongation | Tear Strength (g/mm$^2$) | $O_2$ ($\times 10^{10}$ Dk)* | % Hydration | Tensile at Break ($\times 10^{-6}$ dynes/cm$^2$) |
|---|---|---|---|---|---|---|---|---|
| A | DMA 51.22<br>TSMAA 43.38<br>TEGDMA 0.99<br>BME 0.41<br>MP 4.01 | 0.48 | 1.60 ± 50 | 301 ± 0.08 | 3.89 ± 0.61 | 43 | 50.3 ± 0.3 | 8.9 ± 2.2 |
| B | DMA 50.54<br>TSMAA 43.05<br>TEGDMA 2.02<br>BME 0.41<br>MP 3.98 | 0.992 | 4.54 ± 0.27 | 172 ± 18 | 2.38 ± 0.31 | 35 | 48.2 ± 0.1 | 13.7 ± 3.3 |
| C | DMA 50.19<br>TSMAA 42.77<br>TEGDMA 2.56<br>BME 0.42<br>MP 4.06 | 1.26 | 5.76 ± 0.32 | 129 ± 6 | 2.23 ± 0.19 | 38 | 47.8 ± 1.4 | 11.6 ± 1.1 |
| D | DMA 50.02<br>TSMAA 42.46<br>TEGDMA 3.03<br>BME 0.40<br>MP 4.09 | 1.50 | 7.12 ± 0.50 | 107 ± 10 | 2.03 ± 0.41 | 39 | 47.1 ± 0.2 | 10.2 ± 2.0 |
| E | DMA 49.29<br>TSMAA 41.80<br>TSMAA Dimer 4.49<br>BME 0.40<br>MP 4.01 | 1.09 | 5.54 ± 0.24 | 146 ± 33 | 4.03 ± 1.0 | 41 | 45.5 ± 0.2 | 11.8 ± 3.4 |
| F | DMA 48.85<br>TSMAA 41.16<br>TSMAA Dimer 5.59<br>BME 0.41<br>MP 3.99 | 1.37 | 7.72 ± 0.30 | 114 ± 12 | 3.07 ± 0.31 | 38 | 43.6 ± 0.3 | 11.8 ± 2.0 |
| G | DMA 48.18<br>TSMAA 40.62<br>TSMAA Dimer 6.72<br>BME 0.40<br>MP 4.09 | 1.66 | 9.81 ± 0.62 | 83 ± 9 | 2.93 ± 0.32 | 37 | 41.7 ± 0.1 | 10.0 ± 1.9 |
| H | DMA 50.86<br>TSMAA 43.42<br>EGDMA 1.08<br>BME 0.41<br>MP 4.22 | 0.886 | 4.31 ± 0.12 | 153 ± 8 | 2.31 ± 0.37 | 38 | 46.7 — 48.1 | 11.0 ± 1.5 |
| I | DMA 50.98<br>TSMAA 43.25<br>EGDMA 1.37<br>BME 0.41 | 1.12 | 6.42 ± 0.30 | 116 ± 7 | 2.17 ± 0.13 | 39 | 43.2 — 45.7 | 10.9 ± 1.6 |

TABLE XII-continued

Physical Properties of 5/1 MOLE RATIO DMA/TSMAA Copolymers
With Changes In Crosslinker Concentration

| Sample | Wt. % Formulation | Mole % X-LINKER | Modulus ($\times 10^{-6}$ dynes/cm$^2$) | % Elongation | Tear Strength (g/mm$^2$) | O$_2$ ($\times 10^{10}$ Dk)* | % Hydration | Tensile at Break ($\times 10^{-6}$ dynes/cm$^2$) |
|---|---|---|---|---|---|---|---|---|
| J | MP 4.00 DMA 50.68 TSMAA 43.20 EGDMA 1.67 BME 0.41 | 1.36 | 8.96 ± 0.79 | 92 ± 6 | 1.64 ± 0.12 | 38 | 41.8 − 42.9 | 10.4 ± 2.0 |
| K | MP 4.11 DMA 50.67 TSMAA 42.91 TMPTMA 1.97 BME 0.41 | 0.933 | 7.57 ± 0.59 | 110 ± 7 | 2.00 ± 0.31 | 40 | 46.5 ± 0.3 | 12.5 ± 2.1 |
| L | MP 4.04 DMA 50.21 TSMAA 42.72 TMPTMA 2.51 BME 0.41 | 1.20 | 11.23 ± 0.93 | 67 ± 10 | 1.93 ± 0.13 | 38 | 44.5 ± 0.3 | 9.5 ± 1.8 |
| M | MP 4.15 DMA 50.08 TSMAA 42.43 TMPTMA 2.99 BME 0.40 | 1.43 | 15.05 ± 1.5 | 62 ± 9 | 1.85 ± 0.09 | 34 | 41.9 ± 0.4 | 10.9 ± 1.7 |
| N | MP 4.01 DMA 50.26 TSMAA 42.89 MAPTMS Dimer 2.37 BME 0.41 | 1.00 | 3.15 ± 0.19 | 240 ± 18 | 3.10 ± 0.36 | 36 | 48.1 ± 0.5 | 16.3 ± 3.7 |
| O | MP 4.06 DMA 49.95 TSMAA 42.47 MAPTMS Dimer 3.19 BME 0.40 | 1.34 | 6.68 ± 0.58 | 141 ± 15 | 2.87 ± 0.44 | 38 | 43.5 | 14.2 ± 2.7 |
| P | MP 3.98 DMA 49.52 TSMAA 42.11 MAPTMS Dimer 3.91 BME 0.40 MP 4.05 | 1.66 | 9.44 ± 0.38 | 104 ± 6 | 2.65 ± 0.43 | 36 | 43.8 | 13.5 ± 1.3 |

*Dk unit = cm$^3$(O$_2$) · cm/cm$^2$ · sec · cm Hg

EXAMPLE XXVIII

A series of copolymers were prepared according to the present invention, varying the mole ratio of the DMA and TSMAA comonomers from 3:1 to 5:1. The contact angles were determined for these copolymers using the Wilhelmy Plate method; the results are reported in Table XIII. Within the tested range there does not appear to be any significant difference in contact angles. The advancing angle is 60°–75° and the receding angle is less than 10°. The contact angle measured by Sessile Drop is 75°–82° for 5/1 DMA/TSMAA molded lenses.

TABLE XIII

Contact Angles of DMA/TSMAA Copolymers

| Sample ID | Mole Ratio DMA:TSMAA | Contact Angle Advancing | Receding |
|---|---|---|---|
| A | 3:1 | 76 | <10 |
| B | 3.5:1 | 61 | <10 |
| C | 4:1 | 64 | <10 |
| D | 5:1 | 63 | <10 |
| E | 1:0 | 10 | <10 |
| F | polyHEMA | 60 | <15 |
| G | crofilcon A | 43 | <10 |

EXAMPLE XXIX

The DMA/TSMAA copolymer was fabricated into molded lenses which were studied for in vitro protein deposition properties. The in vitro coating of DMA/TSMAA molded lenses was found to be comparable to HEMA lenses. As shown in Table XIV, the amount of coating was reduced as the wt. % TEGDMA (tetraethylene glycol dimethacrylate) cross-linker increased from 2.0% to 2.5% by weight.

TABLE XIV

PROTEIN DEPOSITION AS A FUNCTION OF WT %
TEGDMA CROSSLINKER IN DMA/TSMAA
(5/1 MOLAR RATIO) MOLDED LENSES

| Crosslinker (%) | Protein Deposition (ng/mm$^2$) |
|---|---|
| 2.0 | 700 ± 20 |
| 2.5 | 550 ± 90 |

Table XV shows that as the molar ratio of DMA/TSMAA varied from 1:0 to 1:1 ratio, the in vitro coatings on these lenses were reduced by the addition of a comonomer of the present invention. The lowest amount of in vitro protein deposition was found in 1:1 DMA/TSMAA molded lenses; this was comparable to the protein deposition on polyHEMA (500±100 ng/mm$^2$) which is a moderate water content material.

TABLE XV
INFLUENCE OF POLYMER COMPOSITION ON PROTEIN DEPOSITION

| Material (Molar Ratio) | Protein Deposition (ng/mm$^2$) |
|---|---|
| perfilcon A | 3300 |
| crofilcon A | 680 ± 100 |
| polyDMA | 610 ± 60 |
| DMA/TSMAA (5/1) | 550 ± 60 |
| DMA/TSMAA (1/1) | 500 ± 60 |
| polyHEMA | 500 ± 100 |

EXAMPLE XXX

A copolymer of DMA and TSMAA was prepared according to the present invention, and characterized in terms of percent elongation, tear strength, and percent conversion. The effect of the crosslinker tetraethyleneglycol dimethacrylate (TEGDMA) on the physical properties, such as tear strength and percent elongation was investigated, along with how these properties affect lens performance.

The physical properties of 5/1 DMA/TSMAA molar ratio formulation with 0.6% and 1.0% TEGDMA (by wt.) were measured. The 1.0% TEGDMA formulation elongated less and was stronger than the 0.6% TEGDMA formulation. However, both formulations elongated well above the elongation for a polyHEMA lens, and also maintained greater tear strength.

EXAMPLE XXXI

Copolymers were prepared using TSMAA and MMA, with MAA as a third comonomer. The level of methacrylic acid (MAA) in the TSMAA/MMA copolymers was varied. It was found that the addition of MAA effectively reduces the contact angle of the material. Films were cast containing 12% and 20% methacrylic acid, and 0.5% tetraethyleneglycoldimethacrylate (TEGDMA), with TSMAA and MAA making up the balance. One series was irradiated on with a UV lamp for two hours (with a lamp distance of six inches) followed by a 24-hour postcure at 120° C. Another identical series was thermally polymerized in an oven for 24 hours at 70° C., followed by a postcure at 120° C. for 24 hours. Differences were found at the 20% methacrylic acid level between the UV-initiated and thermally polymerized copolymer. The UV copolymer was opaque and the thermal copolymer had only a slight opacity.

EXAMPLE XXXII

Polymers and various copolymers listed in Table XVI were prepared from TSMAA. Wetting properties were measured by the Wilhelmy Plate method and are shown in Table XVI.

The addition of methacrylic acid to copolymers of TSMAA and hydroxyethyl methacrylate were investigated. The addition of 5% methacrylic acid to a 40% TSMAA copolymer caused the percent hydration to change from 20% to 52% and the oxygen permeability to decrease from a Dk of 43 to $36 \times 10^{-10}$ cm$^3$(O$_2$)·cm/cm$^2$·sec·cm Hg.

TABLE XVI
PROPERTIES OF TSMAA COPOLYMERS

| TSMAA | Comonomer | % MAA | % TEGDMA | % Hydration | Dk | θ A | θ R |
|---|---|---|---|---|---|---|---|
| 20% | HEMA | 0 | 1.0 | 25.6 | — | — | — |
| 40% | HEMA | 0 | 1.0 | 22.5 | 43.3 | 63 | 15 |
| 80% | HEMA | 0 | 1.0 | 0 | 22.1 | — | — |
| 40% | HEMA | 0 | .5 | 19.5 | 42.1 | — | — |
| 40% | HEMA | 5 | .5 | 51.8 | 36.4 | — | — |
| 40% | HEMA | 10 | .5 | 58.2 | 35.2 | — | — |
| 35% | MMA | 0 | 2.7 | — | 16.8 | 70 | 25 |
| 40% | MMA | 0 | 2.7 | — | — | 75 | 22 |
| 45% | MMA | 0 | 2.7 | — | 20.5 | 80 | 34 |
| 40% | MMA | 5 | 2.7 | — | 20.5 | 70 | 22 |
| 100% | — | 0 | 1.0 | — | 51.7 | — | — |
| 100% | — | 0 | 0 | — | 81.7 | — | — |

EXAMPLE XXXIII

A series of polymers were prepared using TSMAA with NVP and/or DMA as comonomers. All of the polymers in this series were clear, indicating that DMA/TSMAA and DMA/NVP/TSMAA comonomers are very compatible and form a homogeneous copolymer matrix. These copolymers can be used to fabricate extended wear contact lenses due to their excellent optical clarity, oxygen permeability and strength. Presented in Tables XVII and XVIII are the oxygen permeability, tear strength and wetting angle data obtained on these polymer systems.

The relationship between oxygen permeability and water content is illustrated in Table XVII. Oxygen permeability, for copolymers with increasing mole ratios of DMA to TSMAA, is shown to decrease as the water content increases. This is presumably due to the relative oxygen permeabilities of siloxanes and water.

As shown in Table XVIII, oxygen permeability is higher in the terpolymer having a higher concentration of TSMAA vis a vis the other comonomers tested. Water content increases by incorporating more of the DMA/NVP comonomers. Contact angles were also measured and are reported in Table XVIII.

TABLE XVII
Properties of DMA/TSMAA Copolymer

| Formulas (Mole Ratio) | % Water | *Dk × 10$^{10}$ | Tear Strength (g/mm$^2$) | Wetting Angle Adv. θ | Rec. θ | Comments |
|---|---|---|---|---|---|---|
| $\frac{3}{1} = \frac{DMA}{TSMAA}$ | 21.9 | 41.6 | 7.1 | 85° | 34° | clear, strong nonelastic |

TABLE XVII-continued

Properties of DMA/TSMAA Copolymer

| Formulas (Mole Ratio) | % Water | *Dk × $10^{10}$ | Tear Strength (g/mm²) | Wetting Angle Adv. θ | Wetting Angle Rec. θ | Comments |
|---|---|---|---|---|---|---|
| $\frac{5}{1} = \frac{DMA}{TSMAA}$ | 33.9 | 37.9 | 6.0 | 85° | 34° | clear, strong min elasticity |
| $\frac{7}{1} = \frac{DMA}{TSMAA}$ | 40.4 | 30.1 | 3.8 | 78° | 34° | clear, strong elastic |

*The units of Dk = $cm^3(O_2) \cdot cm/cm^2 \cdot sec \cdot cm\ Hg$
All formulas contain 0.3% TEGDMA and 0.4% BME

TABLE XVIII

Properties Of DMA/NVP/TSMAA Terpolymer

| Formulas (Mole Ratio)* | Wt. % DMA/NVP Comonomers | % Water | **Dk × $10^{10}$ | Tear Strength (g/mm²) | Wetting Angle Adv. θ | Wetting Angle Rec. θ | Comments |
|---|---|---|---|---|---|---|---|
| $\frac{7}{1} = \frac{DMA}{NVP}$ / TSMAA | DMA 32.2  NVP 30.0 | 54.0 | 36.7 | 2.5 | 71° | 11° | slightly hazy very elastic |
| $\frac{9}{1} = \frac{DMA}{NVP}$ / TSMAA | DMA 47.9  NVP 20.0 | — | — | — | 67° | 16° | clear, elastic |
| $\frac{9}{1} = \frac{DMA}{NVP}$ / TSMAA | DMA 42.9  NVP 25.0 | 54.6 | 32.9 | 2.1 | 47° | 10° | clear, elastic |
| $\frac{9}{1} = \frac{DMA}{NVP}$ / TSMAA | DMA 37.9  NVP 30.0 | 58.0 | 32.6 | 2.0 | — | — | clear, elastic |

*Ratio of moles of DMA/NVP comonomers to moles of TSMAA
**Dk unit = $cm^3(O_2) \cdot cm/cm^2 \cdot sec \cdot cm\ Hg$
All formulas contain 0.3% TEGDMA and 0.4% BME

EXAMPLE XXXIV

Polymers were prepared from TSMAA to determine physical properties of various systems. Copolymers with MMA were made to provide a comparison to Tris(trimethylsiloxy)silylpropyl methacrylate (TSPMA). Thin films of homo TSMMA and homo TSMAA were prepared for comparison purposes. Copolymers with HEMA and glyceryl methacrylate (GMA) were also prepared. The results are summarized in Tables XIX–XXI, and each of these groups of polymers will be discussed separately.

Homopolymers of TSMAA and TSMMA were prepared for comparison purposes. These results are shown in Table XX. The TSMAA homopolymers tend to be brittle.

TSMAA copolymers were prepared containing 20, 40, 60 and 80% GMA and HEMA. The GMA copolymers with TSMAA were opaque, both in the dry and the hydrated states, and therefore, these particular copolymer formulations are not suitable for contact lenses. When hydrated, all of the HEMA/TSMAA copolymers were clear, or only slightly hazy. The properties of these materials are given in Table XXI.

TABLE XIX

Properties Of Copolymers With MMA

| % Monomer | Type | % TEGDMA | Modulus (× $10^{-10}$ dyne/cm²) | Dk | Receding Contact Angle |
|---|---|---|---|---|---|
| 35% | TSMAA | 2.7% | 1.88 | 16.8 | 25° |
| 40% | TSMAA | 2.7% | — | — | 21° |
| 40% | TSMAA w/5% MAA | 2.7% | 1.97 | 20.5 | 22° |
| 45% | TSMAA | 2.7% | 1.49 | 20.5 | 25° |
| 40% | TSMMA w/5% MAA | 2.7% | 1.91 | 21.0 | 28° |
| — | PMMA | — | 3.0 | ≈0 | 22° |

TSMAA copolymerized with MMA has similar mechanical properties and oxygen permeability to TSMMA copolymers of the same composition, as shown in Table XIX. The major difference between the polymers is in their wettability. The 40% TSMAA copolymers have similar wetting properties to PMMA, whereas even with 5% MAA, TSMMA has about a 25% higher receding contact angle.

TABLE XX

Properties Of Homopolymers Of TSMAA And TSMMA

| Monomer Type | % TEGDMA | Dk | Modulus (dyne/cm²) | Tg (°C.) |
|---|---|---|---|---|
| TSMAA | 1.0% | 51.7 | 5.2 × $10^9$ | 63 |
| TSMAA | 0.0% | 81.7 | — | 48 |
| TSMMA | 1.0% | 82.7 | 5.5 × $10^7$ | −2 |
| TSMMA | 0.0% | Too flexible to test | | |

TABLE XXI

Properties Of Copolymers With HEMA

| % TSMAA | Dk | Modulus (× $10^{-10}$ dyne/cm$^2$) | Receding Contact Angle | % Hydration | Appearance on Hydration | Appearance Dry |
|---|---|---|---|---|---|---|
| 20% | — | — | — | 25.6% | Sl. Hazy | Opaque |
| 40% | 43.4 | .37 | 15° | 22.5% | Clear | Opaque |
| 60% | — | — | — | 19.2% | Clear | Opaque |
| 80% | 22.4 | 1.6 | Sample Crumbled | — | Clear | Sl. Hazy |

EXAMPLE XXXVI

TSAA was synthesized according to Example III (its purity was >97%) and copolymerized with MMA, DMA, TEGDMA, MP and BME. The DMA was used without purification. The methacrylic acid (purity 98%) was used without removing the inhibitor and without purification. The cross-linker, tetraethylene glycol dimethacrylate was used after removing the inhibitors. The N-methyl-2-pyrrolidone and benzoin methyl ether were used without purification.

The TEGDMA, MP and DMA were weighed into a test tube. The weighed amount of TSAA and BME were added to the above mixture and stirred. The mixture was filtered through an HPLC nylon filter (pore size=5.0 μm). Approximately 13 drops of the mixture were syringed into plastic molds. The photopolymerization was carried out under UV radiation, 8 to 14.52 mW/sq.cm. at 365 nm for 60 minutes.

The sample lenses were hydrated in deionized water for at least one hour, followed by overnight immersion in a methanol/water mixture (50/50 by volume). They were then soaked in a standard saline solution. The samples immersed in the saline solution were tested, including contact angle measurement (with and without cleaning the lenses).

In addition to determining the influence of increasing mole percent of TSAA (see Table XXII) and TEGDMA (see Table XXIII) on the properties of the hydrogel, the effect on the wetability of the lenses by adding MAA, a termonomer, to a DMA/TSAA (5:1 mole ratio) mixture was evaluated (see Table XXIV). The MP level in the monomer mixture was raised from 4 t0 10% (by weight) to obtain a more homogeneous polymerization, resulting in higher conversion and uniform structure (see Table XXV). The effect of all the variables on the properties is described below.

A. Conversion

A quantitative conversion of all the monomers, i.e., DMA, TSAA and MAA, was achieved under UV radiation ($\simeq$8 to 14.5 mW/cm$^2$) for the exposure time of approximately 60 minutes. This is in contrast to the case of the DMA/TSMAA copolymers which had TSMAA conversions between 97 and 98%.

In a separate set of experiments, exposure time was gradually reduced from $\simeq$80 to 24 minutes and the conversions for both the DMA and TSAA monomers were still better than 99 and 99.5%, respectively. However, in another experiment at lower UV levels ($\simeq$0.7 to 4.52 mW/cm$^2$) the conversion for DMA was >99% irrespective of exposure time, but the conversion for TSAA was only 89% and continued to decrease with the decrease in exposure time. The incomplete conversion of the TSAA from the monomer mixture indicated that its rate of copolymerization was slower than that of DMA.

B. Hydration and O$_2$-Permeability

The percent hydration decreased with the increase of TSAA content in the copolymer; the results of this evaluation are reported in Table XXII. The oxygen-permeability was higher for the copolymer containing the larger mole percent of TSAA, which may be due to the higher O$_2$-permeability of siloxane.

The decrease in the percent hydration and consequently in the O$_2$-permeability was marginal in the copolymers with the higher TEGDMA content (see Table XXIII). However, a significant increase in percent hydration and O$_2$-permeability was observed when MAA was incorporated into the formulation (see Table XXIV).

TABLE XXII

Properties Of The Copolymer Of DMA/TSAA Containing Various Mole % Of TSAA And 0.48 Percent 0f TEGDMA

| TSAA Mole % | % Conversion DMA | % Conversion TSAA | Hydration % | O$_2$ Permeability × $10^{10}$ Dk*** | Contact Angle Degrees | Tear Strength g/mm$^2$ | Modulus × $10^{-6}$ dynes/cm$^2$ | Tensile at Break × $10^{-6}$ dynes/cm$^2$ | Elongation % |
|---|---|---|---|---|---|---|---|---|---|
| 16.7 | 99 | 99.5 | 51 ± 0.7 | 49 | 73 ± 2 | 5.3 ± 0.9 | 3.7 ± 0.6 | 12.9 ± 1.5 | 314 ± 20 |
| 20.0 | 99 | 99.5 | 46 ± 0.6 | 39 | — | 5.2 ± 1.0 | 2.5 ± 0.4 | 15.0 ± 4.5 | 345 ± 52 |
| 25.0 | 99 | 99.5 | 37 ± 1.3 | 49 | — | Too Elastic | 4.1 ± 1.2 | 16.6 ± 2.4 | Too elastic |
| p(HEMA) | — | — | 38 | 12 | 55/10** | 2.75 ± .25 | 14.0 | 7.0 ± 1.0 | 160 ± 20 |

*Measured by the Sessile Drop Test on lenses which were not cleaned.
**Measured by the Wilhelmy Plate Method on lenses which were cleaned.
***Dk unit = cm$^3$(O$_2$) · cm/cm$^2$ · sec · cm Hg

TABLE XXIII

Properties Of The Copolymer Of DMA/TSAA (5/1) Crosslinked With Varying Amounts Of TEGDMA

| TEGDMA Mole % | % Conversion DMA | % Conversion TSAA | Hydration % | O$_2$ Permeability Dk × $10^{10}$*** | Contact Angle Degrees | Tear Strength g/mm$^2$ | Modulus × $10^{-6}$ dynes/cm$^2$ | Tensile at Break × $10^{-6}$ dynes/cm$^2$ | Elongation % |
|---|---|---|---|---|---|---|---|---|---|
| 0.48 | 99 | 99.5 | 51 ± 0.7 | 40 | 73 ± 2 | 5.3 ± 0.9 | 3.7 ± 0.6 | 12.9 ± 1.5 | 314 ± 20 |
| 0.94 | 99 | 99.7 | 49 ± 1.3 | 42 | 77.5 ± 2.3* | 1.9 ± 0.3 | 5.9 ± 0.3 | 7.6 ± 0.3 | 136 ± 2 |

TABLE XXIII-continued

Properties Of The Copolymer Of DMA/TSAA (5/1)
Crosslinked With Varying Amounts Of TEGDMA

| TEGDMA Mole % | % Conversion DMA | TSAA | Hydration % | $O_2$ Permeability $Dk \times 10^{10}$*** | Contact Angle Degrees | Tear Strength $g/mm^2$ | Modulus $\times 10^{-6}$ dynes/cm$^2$ | Tensile at Break $\times 10^{-6}$ dynes/cm$^2$ | Elongation % |
|---|---|---|---|---|---|---|---|---|---|
| 1.4 | 99 | 99.3 | 47 ± 0.5 | 37 | 80.0 ± 5.9* | 1.3 ± 0.2 | 6.9 ± 0.3 | 6.9 ± 2.4 | 92 ± 20 |

*Measured by the Sessile Drop Test on lenses which were not cleaned.
**Measured by the Wilhelmy Plate Method on lenses which were cleaned.
***Dk unit = cm$^3$(O$_2$) · cm/cm$^2$ · sec · cm Hg

TABLE XXIV

Properties Of The Terpolymer Of DMA/TSAA/MAA (5/1/X)
Crosslinked with TEGDMA (1%)

| MAA Mole % | % Conversion DMA | TSAA | Hydration % | $O_2$ Permeability $DK \times 10^{10}$*** | Contact Angle Degrees | Tear Strength $g/mm^2$ | Modulus dynes/cm$^2$ $\times 10^{-6}$ | Tensile at Break dynes/cm$^2 \times 10^{-6}$ | Elongation % |
|---|---|---|---|---|---|---|---|---|---|
| 0.0 | 99 | 99.5 | 51 ± 0.7 | 40 | 73 ± 2 | 5.3 ± 0.9 | 3.7 ± 0.6 | 12.9 ± 1.5 | 314 ± 20 |
| 4.1 | 99 | 99.5 | 64 ± 0.2 | 50 | 71 ± 0.5 | 1.6 ± 0.3 | 3.0 ± 0.8 | 5.4 ± 1.1 | 257 ± 68 |
| 8.2 | 99 | 99.0 | 73 ± 0.3 | 53 | 68 ± 1 | 1.1 ± 0.2 | 1.6 ± 0.2 | 2.2 ± 0.2 | 173 ± 13 |
| p(HEMA) | — | — | 38 | 12 | 55/10** | 2.75 ± .25 | 14.0 | 7.0 ± 1.0 | 160 ± 20 |

*Measured by the Sessile Drop Test on lenses which were not cleaned (except polyHEMA)
**Measured by the Wilhelmy Plate Method on lenses which were cleaned.
***Dk unit = cm$^3$(O$_2$) · cm/cm$^2$ · sec · cm Hg

TABLE XXV

Properties Of The Copolymer Of DMA/TSAA Crosslinked With TEGDMA (1%)
And Containing Varying Amounts Of N—Methyl-2-Pyrrolidone As A Diluent

| MP-Wt. % | % Conversion DMA | TSAA | Hydration % | $O_2$ Permeability $\times 10^{10}$ Dk*** | Contact Angle Degrees | Tear Strength $g/mm^2$ | Modulus dynes/cm$^2$ $\times 10^{-6}$ | Tensile at Break dynes/cm$^2 \times 10^{-6}$ | Elongation % |
|---|---|---|---|---|---|---|---|---|---|
| 4.0 | 99 | 99.5 | 51 ± 0.7 | 40 | 73 ± 2 | 5.3 ± 0.9 | 3.7 ± 0.6 | 12.9 ± 1.5 | 314 ± 20 |
| 10.0 | 99 | 99.5 | 54 ± 0.7 | 48 | 69 ± 2 | 4.4 ± 0.4 | 3.8 ± 1.5 | 9.6 ± 2.4 | 399 ± 37 |
| 15.0 | 99 | 99.0 | 53 ± 0.7 | 43 | 72.5 ± 0.5* | 3.8 ± 0.5 | 2.5 ± 0.3 | 8.3 ± 3.4 | 374 ± 71 |
| p(HEMA) | — | — | 38 | 12 | 55/10** | 2.75 ± 0.25 | 14.0 | 7.0 ± 1.0 | 160 ± 20 |

*Measured by the Sessile Drop Test on lenses which were not cleaned (except polyHEMA)
**Measured by the Wilhelmy Plate Method on lenses which were cleaned.
***Dk unit = cm$^3$(O$_2$) · cm/cm$^2$ · sec · cm Hg

C. Mechanical Properties

The increasing mole percent of the TSAA in the copolymer did not give significantly different values of the modulus, tear strength, tensile at break and elongation, except that the copolymer containing 25 mole percent of TSAA was very elastic. The increase of TEGDMA content from 0.5 to 1.4 mole percent on the DMA/TSAA copolymer (5:1 mole ratio) deteriorated the tear strength and tensile at break, whereas the modulus increased and the percent elongation decreased from 314 to 92%. A significant drop in all the mechanical properties was observed when MAA was used as one of the monomers in the formulation. Only a marginal loss of mechanical properties was observed when the polymerization of DMA/TSAA (5:1 mole ratio) was conducted with 10% (by weight) of MP. The mechanical properties of both the DMA/TSMAA and DMA/TSAA copolymers are similar.

D. Surface Properties

The contact angles reported in Tables XXII–XXV were measured by the Sessile Drop Test Method on lenses before and after cleaning. The contact angle values lower by 2° and 5° for the terpolymer containing 4.1 and 8.2 mole percent, respectively, of MAA. The drop in the contact angle was insignificant, especially in light of the loss of mechanical properties. A similar decrease in the contact angle (4°) was observed when 10%, instead of the usual 4%, of MP was used, without much affecting the other mechanical properties.

While the present invention has been described with reference to specific embodiments thereof, it should be understood by those skilled in the art that various changes may be made and equivalents may be substituted without departing from the true spirit and scope of the invention. All such modifications are intended to be within the scope of the claims appended hereto.

What is claimed is:

1. A non-fibrous polymeric contact lens material having improved oxygen permeability and stability, said polymeric contact lens material comprising a monomer having the following structural formula:
   first portion for increasing wettability, said first portion being hydrophilic and including a side-chain functionality selected from the group including the following structural formulae:

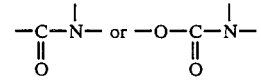

and
   a second portion for increasing oxygen permeability, said second portion including a siloxane;

wherein: said material has a water content of about 15-60%; DK greater than or equal to about $25 \times 10^{-10}$; tear strength greater than or equal to about 1.0 g/mm$^2$; and percent elongation greater than or equal to about 80%.

2. The contact lens material of claim 1 wherein said first portion comprises an acrylamide or a methacrylamide.

3. The contact lens material of claim 1 wherein said second portion comprises an alkyl siloxane.

4. The contact lens material of claim 2 wherein said second portion comprises an alkyl siloxane.

5. The contact lens material of claim 1 wherein said first portion comprises the following structural formula:

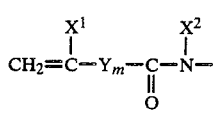

wherein:
$X^1$ is CH$_3$ or H;
$X^2$ is CH$_3$ or H;
m is 0 or 1; and
Y is selected from the group consisting of the following structural formulae, the radical shown on the left of each formula being bonded to the carbon shown on the left of Y in the above formula:

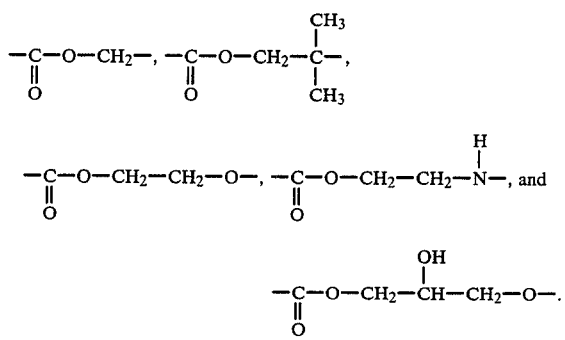

6. The contact lens material of claim 1 wherein said first portion comprises the following structural formula:

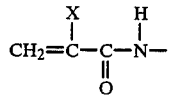

wherein X is CH$_3$ or H.

7. The contact lens material of claim 1 wherein said second portion comprises the following structural formula:

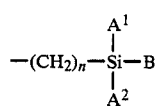

wherein:
n is an integer from 1 to 6;
$A^1$ and $A^2$ are the same or different and are selected from lower alkyl and B groups; and B has the following structural formula:

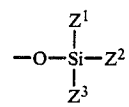

wherein:
$Z^1$, $Z^2$ and $Z^3$ are the same or different and are selected from the group consisting of lower alkyl, phenyl, benzyl and tri-alkylsiloxy substituents.

8. The contact lens material of claim 5 wherein said second portion comprises the following structural formula:

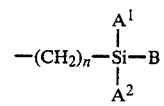

wherein:
n is an integer from 1 to 6;
$A^1$ and $A^2$ are the same or different and are selected from lower alkyl and B groups; and
B has the following structural formula:

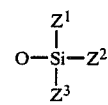

wherein:
$Z^1$, $Z^2$ and $Z^3$ are the same or different and are selected from the group consisting of lower alkyl, phenyl, benzyl and tri-alkylsiloxy substituents.

9. The contact lens material of claim 7 wherein: n is 3; and $Z^1$, $Z^2$ and $Z^3$ are lower alkyl.

10. The contact lens material of claim 8 wherein: n is 3; and $Z^1$, $Z^2$ and $Z^3$ are lower alkyl.

11. The contact lens material of claim 9 wherein $Z^1$, $Z^2$ and $Z^3$ are CH$_3$.

12. The contact lens material of claim 10 wherein $Z^1$, $Z^2$ and $Z^3$ are CH$_3$.

13. The contact lens material of claim 6 wherein said second portion has the following structural formula:

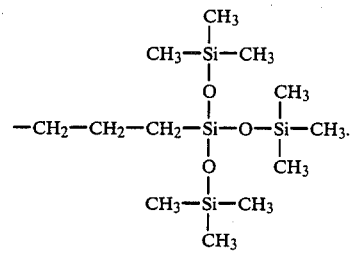

14. A contact lens formed from the contact lens material of claim 1.

15. A contact lens formed from the contact lens material of claim 5.

16. A contact lens formed from the contact lens material of claim 7.

17. A contact lens formed from the contact lens material of claim 8.

18. A contact lens formed from the contact lens material of claim 13.

19. A non-fibrous polymeric material for making a contact lens with improved oxygen permeability and stability, said contact lens material comprising a monomer having the following structural formula:

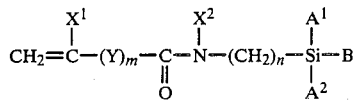

wherein:
 X¹ is CH₃ or H;
 X² is CH₃ or H;
 m is 0 or 1; and
 Y is selected from the group consisting of the following structural formulae, the radical shown on the left of each formula being bonded to the carbon shown on the left of Y in the above formula;

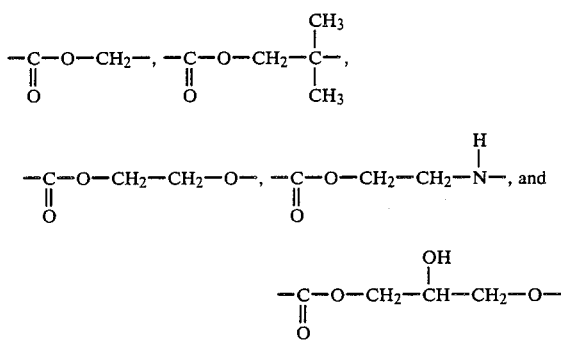

wherein:
 n is an integer from 1 to 6;
 A¹ and A² are the same or different and are selected from lower alkyl and B groups; and
 B has the following structural formula:

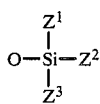

wherein:
 Z¹, Z² and Z³ are the same or different and are selected from the group consisting of lower alkyl, phenyl, benzyl and tri-alkyl-siloxy substituents;
 and
wherein: said material has a water content of about 15-60%; DK greater than or equal to about 25×10⁻¹⁰; tear strength greater than or equal to about 1.0 g/mm²; and percent elongation greater than or equal to about 80%.

20. The contact lens material of claim 19 wherein: m is 0; n is 3; and Z¹, Z² and Z³ are CH₃.

21. The contact lens material of claim 20 wherein X¹ is CH₃.

22. The contact lens material of claim 20 wherein X² is H.

23. The contact lens material of claim 21 wherein X² is H.

24. A contact lens made from the contact lens material of claim 19.

25. A non-fibrous contact lens material for making a contact lens with improved oxygen permeability and stability, said contact lens material comprising a polymer formed from at least a monomer having the following structural formula:

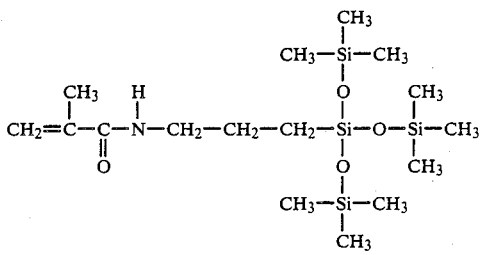

wherein: said material has a water content of about 15-60%; DK greater than or equal to about 24×10⁻¹⁰; tear strength greater than or equal to about 1.0 g/mm²; and percent elongation greater than or equal to about 80%.

26. A non-fibrous contact lens material for making a contact lens with improved oxygen permeability and stability, said contact lens material comprising a polymer formed from at least a monomer having the following structural formula:

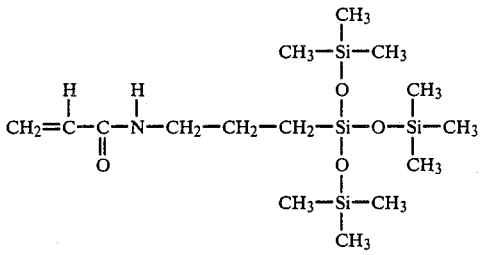

wherein: said material has a water content of about 15-60%; DK greater than or equal to about 25×10⁻¹⁰; tear strength greater than or equal to about 1.0 g/mm²; and percent elongation greater than or equal to about 80%.

27. A non-fibrous contact lens material comprising the copolymerization product of:
 (a) a first monomer having:
  a first portion for increasing wettability, said first portion being hydrophilic and including a sidechain functionality selected from the group consisting of the following structural formulae:

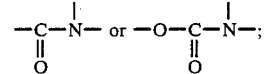

and
  a second portion for increasing oxygen permeability, said second portion including a siloxane;
 (b) a second monomer, copolymerizable with said first monomer;
 (c) a crosslinking agent; and
 (d) a polymerization initiator; and
wherein: said material has a water content of about 15-60%; DK greater than or equal to about 25×10⁻¹⁰; tear strength greater than or equal to about 1.0 g/mm²; and percent elongation greater than or equal to about 80%.

28. The contact lens material of claim 27 comprising the copolymerization product of:
 (a) 30-100 wt/wt% of said first monomer;
 (b) 0-70 wt/wt% of said second monomer;
 (c) 0-10 wt/wt% of said crosslinking agent;
 (d) 0-5 wt/wt% of said polymerization initiator; and
 (e) 0-20 wt/wt% of a diluent.

29. The contact lens material of claim 28 comprising the copolymerization product of:
 (a) 35-45 wt/wt% of said first monomer;
 (b) 45-55 wt/wt% of said second monomer;
 (c) 0-10 wt/wt% of said crosslinking agent;
 (d) 0-5 wt/wt% of said polymerization initiator; and
 (e) 0-10 wt/wt% of a diluent.

30. The contact lens material of claim 28 comprising the copolymerization product of:
 (a) 38-44 wt/wt% of said first monomer;
 (b) 47-52 wt/wt% of said second monomer;
 (c) 3-8 wt/wt% of said crosslinking agent;
 (d) 0-1 wt/wt% of said polymerization initiator; and
 (e) 0-7 wt/wt% of a diluent.

31. The contact lens material of claim 28 comprising the copolymerization product of:
 (a) 41 wt/wt% of said first monomer;
 (b) 49 wt/wt% of said second monomer;
 (c) 5.5 wt/wt% of said crosslinking agent;
 (d) 0.5 wt/wt% of said polymerization initiator; and
 (e) 4.0 wt/wt% of said diluent.

32. The contact lens material of claim 28 wherein said first monomer is N-[tris(trimethylsiloxy)silylpropyl]methacrylamide.

33. The contact lens material of claim 29 wherein said first monomer is N-[tris(trimethylsiloxy)silylpropyl]methacrylamide.

34. The contact lens material of claim 32 wherein said first monomer is N-[tris(trimethylsiloxy)silylpropyl]methacrylamide.

35. The contact lens material of claim 28 wherein said crosslinking agent is 1,3-Bis(methacrylamidopropyl)-1,1,3,3-tetrakis(trimethylsiloxy)disiloxane.

36. The contact lens material of claim 29 wherein said crosslinking agent is 1,3-Bis(methacrylamidopropyl)-1,1,3,3-tetrakis(trimethylsiloxy)disiloxane.

37. The contact lens material of claim 32 wherein said crosslinking agent is 1,3-Bis(methacrylamidopropyl)-1,1,3,3-tetrakis(trimethylsiloxy)disiloxane.

38. The contact lens material of claim 33 wherein said crosslinking agent is 1,3-Bis(methacrylamidopropyl)-1,1,3,3-tetrakis(trimethylsiloxy)disiloxane.

39. The contact lens material of claim 34 wherein said crosslinking agent is 1,3-Bis(methacrylamidopropyl)-1,1,3,3-tetrakis(trimethylsiloxy)disiloxane.

40. The contact lens material of claim 35 wherein said crosslinking agent is 1,3-Bis(methacrylamidopropyl)-1,1,3,3-tetrakis(trimethylsiloxy)disiloxane.

41. The contact lens material of claim 28 wherein said first monomer has the following structural formula:

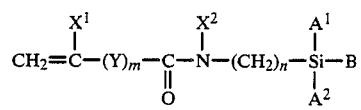

wherein:
 $X^1$ is $CH_3$ or H;
 $X^2$ is $CH_3$ or H;
 m is 0 or 1;
 n is an integer from 1 to 6;
 Y is selected from the group consisting of the following structural formulae, the radical shown on the left of each formula being bonded to the carbon shown on the left of Y in the above formula:

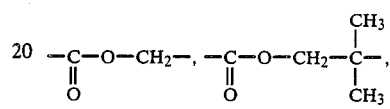

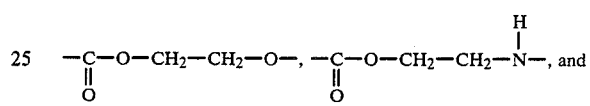

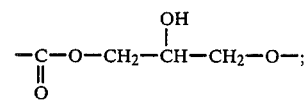

$A^1$ and $A^2$ are the same or different and are selected from lower alkyl and B groups; and
B has the following structural formula:

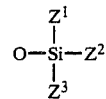

wherein:
 $Z^1$, $Z^2$ and $Z^3$ are the same or different and are selected from the group consisting of lower alkyl, phenyl, benzyl and tri-alkylsiloxy substituents.

42. The contact lens material of claim 41 wherein: m is 0; n is 3; and $Z^1$, $Z^2$ and $Z^3$ are $CH_3$.

43. The contact lens material of claim 42 wherein $X^1$ is $CH_3$.

44. The contact lens material of claim 42 wherein $X^2$ is H.

45. The contact lens material of claim 44 wherein $X^1$ is $CH_3$.

46. The contact lens material of claim 32 wherein said crosslinking agent is ethyleneglycoldimethacrylate or tetraethyleneglycoldimethacrylate.

47. The contact lens material of claim 28 wherein said second monomer is selected from the group consisting of: methyl methacrylate, hydroxyethyl methacrylate, glyceryl methacrylate, N,N-dimethylacrylamide, N-Vinyl pyrrolidone, α-Methylglucoside-6-methacrylate, and methacrylic acid.

48. The contact lens material of claim 27 wherein said crosslinking agent comprises the following structural formula:

$$CH_2=\overset{X^1}{\underset{|}{C}}-Y_m-\underset{\underset{O}{\|}}{C}-\overset{X^2}{\underset{|}{N}}-(CH_2)_n-\underset{\underset{\underset{A^2}{|}}{\overset{\overset{A^2}{|}}{\overset{A^1-Si-A^3}{|}}}}{\overset{|}{\underset{|}{Si}}}-O-\underset{\underset{\underset{A^2}{|}}{\overset{\overset{A^2}{|}}{\overset{A^1-Si-A^3}{|}}}}{\overset{|}{\underset{|}{Si}}}-(CH_2)_n-\overset{X^2}{\underset{|}{N}}-\underset{\underset{O}{\|}}{C}-Y_m-\overset{X^1}{\underset{|}{C}}=CH_2$$

wherein:
$X^1$ is $CH_3$ or H;
$X^2$ is $CH_3$ or H;
m is 0 or 1;
n is an integer from 1 to 6;
$A^1$ to $A^3$ are the same or different and are selected from lower alkyl, phenyl, benzyl, and tri-substituted-siloxy; and
Y is selected from the group consisting of the following structural formulae, the radical shown on the left of each formula being bonded to a carbon bearing an $X^1$ substituent in the above formula:

$$-\underset{\underset{O}{\|}}{C}-O-CH_2-, \quad -\underset{\underset{O}{\|}}{C}-O-CH_2-\overset{\overset{CH_3}{|}}{\underset{\underset{CH_3}{|}}{C}}-,$$

$$-\underset{\underset{O}{\|}}{C}-O-CH_2-CH_2-O-, \quad -\underset{\underset{O}{\|}}{C}-O-CH_2-CH_2-\overset{\overset{H}{|}}{N}-, \text{ and}$$

$$-\underset{\underset{O}{\|}}{C}-O-CH_2-\overset{\overset{OH}{|}}{CH}-CH_2-O-.$$

49. The contact lens material of claim 41 wherein said crosslinking agent comprises the following structural formula:

$$CH_2=\overset{X^1}{\underset{|}{C}}-Y_m-\underset{\underset{O}{\|}}{C}-\overset{X^2}{\underset{|}{N}}-(CH_2)_n-\underset{\underset{\underset{A^2}{|}}{\overset{\overset{A^2}{|}}{\overset{A^1-Si-A^3}{|}}}}{\overset{|}{\underset{|}{Si}}}-O-\underset{\underset{\underset{A^2}{|}}{\overset{\overset{A^2}{|}}{\overset{A^1-Si-A^3}{|}}}}{\overset{|}{\underset{|}{Si}}}-(CH_2)_n-\overset{X^2}{\underset{|}{N}}-\underset{\underset{O}{\|}}{C}-Y_m-\overset{X^1}{\underset{|}{C}}=CH_2$$

wherein:
$X^1$ is $CH_3$ or H;
$X^2$ is $CH_3$ or H;
m is 0 or 1;
n is an integer from 1 to 6;
$A^1$ to $A^3$ are the same or different and are selected from lower alkyl, phenyl, benzyl, and tri-substituted-siloxy; and
Y is selected from the group consisting of the following structural formulae, the radical shown on the left of each formula being bonded to a carbon bearing an $X^1$ substituent in the above formula:

$$-\underset{\underset{O}{\|}}{C}-O-CH_2-, \quad -\underset{\underset{O}{\|}}{C}-O-CH_2-\overset{\overset{CH_3}{|}}{\underset{\underset{CH_3}{|}}{C}}-,$$

$$-\underset{\underset{O}{\|}}{C}-O-CH_2-CH_2-O-, \quad -\underset{\underset{O}{\|}}{C}-O-CH_2-CH_2-\overset{\overset{H}{|}}{N}-, \text{ and}$$

$$-\underset{\underset{O}{\|}}{C}-O-CH_2-\overset{\overset{OH}{|}}{CH}-CH_2-O-.$$

50. A non-fibrous contact lens material having improved oxygen permeability and stability, said contact lens material comprising a polymer formed from at least a monomer having:

a first portion for increasing wettability, said first portion being hydrophilic and including a side-chain functionality selected from the group including the following structural formulae:

$$-\underset{\underset{O}{\|}}{C}-\overset{|}{N}- \quad \text{or} \quad -O-\underset{\underset{O}{\|}}{C}-\overset{|}{N}-$$

and a second portion for increasing oxygen permeability, said second portion including a siloxane;
wherein: said material has a water content of about 15-60%; DK greater than or equal to about $25 \times 10^{-10}$; tear strength greater than or equal to about 1.0 g/mm$^2$; and percent elongation greater than or equal to about 80%.

51. The contact lens material of claim 50 wherein said first portion comprises an acrylamide or a methacrylamide.

52. The contact lens material of claim 50 wherein said second portion comprises an alkyl silyl siloxane.

53. The contact lens material of claim 51 wherein said second portion comprises an alkyl silyl siloxane.

54. The contact lens material of claim 50 wherein said first portion comprises the following structural formula:

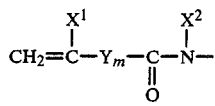

wherein:
X$^1$ is CH$_3$ or H;
X$^2$ is CH$_3$ or H;
m is 0 or 1; and
Y is selected from the group consisting of the following structural formulae, the radical shown on the left of each formula being bonded to the carbon shown on the left of Y in the above formula:

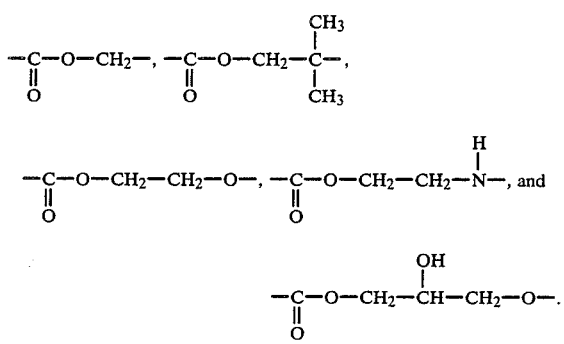

55. The contact lens material of claim 50 wherein said first portion comprises the following structural formula:

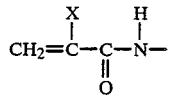

wherein X is CH$_3$ or H.

56. The contact lens material of claim 50 wherein said second portion comprises the following structural formula:

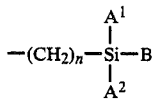

wherein:
n is an integer from 1 to 6;
A$^1$ and A$^2$ are the same or different and are selected from lower alkyl and B groups; and
B has the following structural formula:

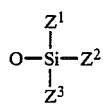

wherein:
Z$^1$, Z$^2$ and Z$^3$ are the same or different and are selected from the group consisting of lower alkyl, phenyl, benzyl and tri-alkylsiloxy substituents.

57. The contact lens material of claim 54 wherein said second portion comprises the following structural formula:

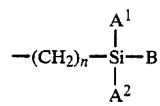

wherein:
n is an integer from 1 to 6;
A$^1$ and A$^2$ are the same or different and are selected from lower alkyl and B groups; and
B has the following structural formula:

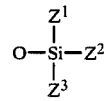

wherein:
Z$^1$, Z$^2$ and Z$^3$ are the same or different and are selected from the group consisting of lower alkyl, phenyl, benzyl and tri-alkylsiloxy substituents.

58. The contact lens material of claim 56 wherein: n is 3; and Z$^1$, Z$^2$ and Z$^3$ are lower alkyl.

59. The contact lens material of claim 57 wherein: n is 3; and Z$^1$, Z$^2$ and Z$^3$ are lower alkyl.

60. The contact lens material of claim 58 wherein Z$^1$, Z$^2$ and Z$^3$ are CH$_3$.

61. The contact lens material of claim 59 wherein Z$^1$, Z$^2$ and Z$^3$ are CH$_3$.

62. The contact lens material of claim 55 wherein said second portion has the following structural formula:

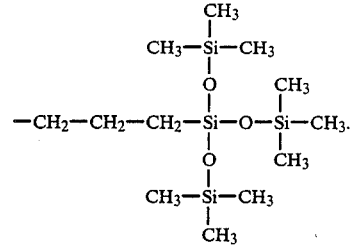

63. A contact lens formed from the contact lens material of claim 50.
64. A contact lens formed from the contact lens material of claim 54.
65. A contact lens formed from the contact lens material of claim 56.
66. A contact lens formed from the contact lens material of claim 57.
67. A contact lens formed from the contact lens material of claim 62.
68. A non-fibrous material for working a contact lens with improved oxygen permeability and stability, said contact lens material comprising a polymer formed from at least a monomer having the following structural formula:

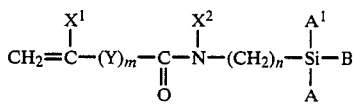

wherein:
X¹ is CH₃ or H;
X² is CH₃ or H;
m is 0 or 1; and
Y is selected from the group consisting of the following structural formulae, the radical shown on the left of each formula being bonded to the carbon shown on the left of Y in the above formula,

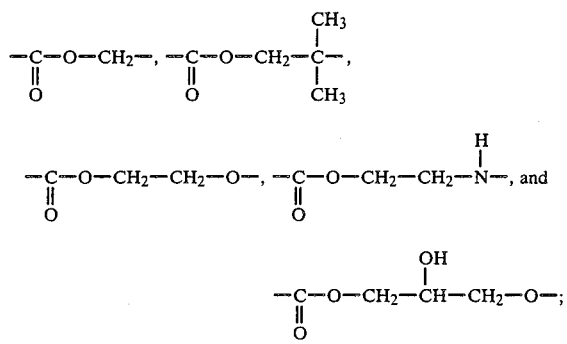

wherein:
n is an integer from 1 to 6;
A¹ and A² are the same or different and are selected from lower alkyl and B groups; and B has the following structural formula:

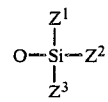

wherein:
$Z^1$, $Z^2$ and $Z^3$ are the same or different and are selected from the group consisting of lower alkyl, phenyl, benzyl and tri-alkyl-siloxy substituents; and
wherein: said material has a water content of about 15–60%; DK greater than or equal to about $25 \times 10^{-10}$; tear strength greater than or equal to about 1.0 g/mm²; and percent elongation greater than or equal to about 80%.

69. The contact lens material of claim 68 wherein: m is 0; n is 3; and $Z^1$, $Z^2$ and $Z^3$ are CH₃.

70. The contact lens material of claim 69 wherein X¹ is CH₃.

71. The contact lens material of claim 69 wherein X² is H.

72. The contact lens material of claim 70 wherein X² is H.

73. A contact lens made from the contact lens material of claim 69.

* * * * *

UNITED STATES PATENT AND TRADEMARK OFFICE
CERTIFICATE OF CORRECTION

PATENT NO.   :   4,711,943

DATED        :   December 8, 1987

INVENTOR(S)  :   Thomas B. Harvey, III

It is certified that error appears in the above-identified patent and that said Letters Patent is hereby corrected as shown below:

Column 35, line 42, "TSPMA" should read --TSMMA--.
Column 33, line 56, delete "on"
Column 21, TABLE IX, the last word in the head "Mexamethyldisilizane" should read --Hexamethyldisilazane--.
Column 14, line 58, "disilizane" should read --disilazane--.
Column 13, line 40, after "acryloyl" insert a period (.).
Column 3, line 24, delete "develop a".

Signed and Sealed this

Twenty-third Day of August, 1988

Attest:

DONALD J. QUIGG

Attesting Officer    Commissioner of Patents and Trademarks

UNITED STATES PATENT AND TRADEMARK OFFICE
CERTIFICATE OF CORRECTION

PATENT NO. : 4,711,943

DATED : December 8, 1987

INVENTOR(S) : Thomas B. Harvey III

It is certified that error appears in the above-identified patent and that said Letters Patent is hereby corrected as shown below:

Column 19, line 57, "diester" should read -- diamide --,

Signed and Sealed this

Fourth Day of October, 1988

Attest:

DONALD J. QUIGG

*Attesting Officer*

*Commissioner of Patents and Trademarks*